United States Patent
Takahashi et al.

(10) Patent No.: US 9,085,772 B2
(45) Date of Patent: Jul. 21, 2015

(54) METHOD FOR SUPPRESSING RECEPTOR TYROSINE KINASE-MEDIATED PRO-SURVIVAL SIGNALING IN CANCER CELL

(75) Inventors: Takashi Takahashi, Nagoya (JP); Tomoya Yamaguchi, Nagoya (JP)

(73) Assignee: NATIONAL UNIVERSITY CORPORATION NAGOYA UNIVERSITY, Aichi-ken (JP)

( * ) Notice: Subject to any disclaimer, the term of this patent is extended or adjusted under 35 U.S.C. 154(b) by 0 days.

(21) Appl. No.: 13/976,186

(22) PCT Filed: Dec. 26, 2011

(86) PCT No.: PCT/JP2011/080083
§ 371 (c)(1),
(2), (4) Date: Sep. 3, 2013

(87) PCT Pub. No.: WO2012/090939
PCT Pub. Date: Jul. 5, 2012

(65) Prior Publication Data
US 2013/0338214 A1    Dec. 19, 2013

(30) Foreign Application Priority Data
Dec. 27, 2010    (JP) ................................ 2010-290373

(51) Int. Cl.
| | | |
|---|---|---|
| *C12Q 1/68* | (2006.01) | |
| *C12N 15/113* | (2010.01) | |
| *A61K 31/7088* | (2006.01) | |
| *C12Q 1/48* | (2006.01) | |
| *G01N 33/50* | (2006.01) | |
| *G01N 33/574* | (2006.01) | |
| *G01N 33/566* | (2006.01) | |
| *A61K 38/22* | (2006.01) | |
| *A61K 35/17* | (2015.01) | |
| *A61K 35/745* | (2015.01) | |

(52) U.S. Cl.
CPC ........ *C12N 15/1137* (2013.01); *A61K 31/7088* (2013.01); *A61K 35/17* (2013.01); *A61K 35/745* (2013.01); *A61K 38/2271* (2013.01); *C12N 15/1138* (2013.01); *C12Q 1/485* (2013.01); *G01N 33/5011* (2013.01); *G01N 33/566* (2013.01); *G01N 33/57407* (2013.01); *G01N 33/57423* (2013.01); *C12N 2310/14* (2013.01); *G01N 2500/00* (2013.01)

(58) Field of Classification Search
None
See application file for complete search history.

(56) References Cited

U.S. PATENT DOCUMENTS

2008/0318212 A1   12/2008  Wilson et al.
2012/0082986 A1*   4/2012  Takahashi et al. ........... 435/6.12

FOREIGN PATENT DOCUMENTS

| WO | 2005100605 | 10/2005 |
| WO | 2006111035 | 10/2006 |
| WO | 2007/146957 A2 | 12/2007 |
| WO | 2008/076868 A2 | 6/2008 |
| WO | 2010/008069 A1 | 1/2010 |
| WO | 2010/124188 A1 | 10/2010 |

OTHER PUBLICATIONS

Jie Zhang, et al., "Src-Family Kinases Are Activated in Non-Small Cell Lung Cancer and Promote the Survival of Epidermal Growth Factor Receptor-Dependent Cell Lines", The American Journal of Pathology, Jan. 2007, pp. 366-376, vol. 170, No. 1.
Jeffrey A. Engelman, et al., "MET Amplification Leads to Gefitinib Resistance in Lung Cancer by Activating ERBB3 Signaling", Science, May 18, 2007, pp. 1039-1043, vol. 316, No. 5827.
Masaru Katoh, "WNT/PCP signaling pathway and human cancer (Review)", Oncology Reports, Dec. 2005, pp. 1583-1588, vol. 14, No. 6.
Gentile Alessandra, et al., "Ror1 is a pseudokinase that is crucial for Met-driven tumorigenesis", Cancer Research, Apr. 15, 2011, pp. 3132-3141, (abstract) Medline [online] Accession No. 2011436696, [retrieved on Jan. 27, 2012]. Retrieved from STN.
Hisaaki Tanaka, et al., "Lineage-Specific Dependency of Lung Adenocarcinomas on the Lung Development Regulator TTF-1", Cancer Research, 2007, pp. 6007-6011, vol. 67, No. 13.
Jude Kendall, et al., "Oncogenic cooperation and coamplification of developmental transcription factor genes in lung cancer", PNAS, Oct. 16, 2007, pp. 16663-16668, vol. 104, No. 42.
Barbara A. Weir., et al., "Characterizing the cancer genome in lung adenocarcinoma", Nature Publishing Group, 2007, pp. 893-898, vol. 450.
Ka Kwei, et al., "Genomic profiling identifies *TITF1* as a lineage-specific oncogene amplified in lung cancer", Oncogene, 2008, pp. 3635-3640, vol. 27.
International Search Report for PCT/JP2011/080083, dated Feb. 7, 2012.
Yamaguchi et al., "NKX2-1/TITF1/TTF-1-Induced ROR1 is required to sustain EGFR survival signaling in lung adenocarcinoma", Cancer Cell, 21(3):348-361 (2012).
Communication for European Patent 11 852 281.2 dated Oct. 27, 2014, with Supplementary European Search Report (dated Oct. 17, 2014).

* cited by examiner

*Primary Examiner* — Tracy Vivlemore
(74) *Attorney, Agent, or Firm* — Sughrue Mion, PLLC

(57) ABSTRACT

In order to provide a screening method for a compound capable of suppressing a mechanism of ROR1 by targeting ROR1 and to provide a drug comprising as an active ingredient a compound capable of suppressing the mechanism, it has been found out that suppressing a function of ROR1 makes it possible to suppress receptor tyrosine kinase-mediated pro-survival signaling in a cancer cell. Further, it has been found out that suppressing a function of ROR1 also effectively suppresses growth of cancer cell lines having acquired resistance to inhibitors of receptor tyrosine kinases such as EGFR and MET.

3 Claims, 8 Drawing Sheets

SEQUENCE LISTING

```
<160> NUMBER OF SEQ ID NOS: 14

<210> SEQ ID NO 1
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 1
gtggtttctt ccactggagt cttgt                                      25

<210> SEQ ID NO 2
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 2
```

```
cgtggtgatg ttattcattg gttca                                            25

<210> SEQ ID NO 3
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 3
atccggattg gaattcccat ggcag                                            25

<210> SEQ ID NO 4
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 4
gaatccatct tcttcatact catct                                            25

<210> SEQ ID NO 5
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 5
gattcaaagg attccaagga gaaga                                            25

<210> SEQ ID NO 6
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 6
cttgtgattt ttatttatag gatct                                            25

<210> SEQ ID NO 7
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 7
tctctctgag cctcggtttc                                                  20

<210> SEQ ID NO 8
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 8
cccccacact cctcaaact                                                   19

<210> SEQ ID NO 9
<211> LENGTH: 21
<212> TYPE: RNA
```

```
<213> ORGANISM: Artificial
<220> FEATURE:
<223> OTHER INFORMATION: Artificially synthesized oligonucleotide
      sequence

<400> SEQUENCE: 9
cagcaaugga uggaauuuca a                                              21

<210> SEQ ID NO 10
<211> LENGTH: 19
<212> TYPE: RNA
<213> ORGANISM: Artificial
<220> FEATURE:
<223> OTHER INFORMATION: Artificially synthesized oligonucleotide
      sequence

<400> SEQUENCE: 10
cccagugagu aaucucagu                                                 19

<210> SEQ ID NO 11
<211> LENGTH: 19
<212> TYPE: RNA
<213> ORGANISM: Artificial
<220> FEATURE:
<223> OTHER INFORMATION: Artificially synthesized oligonucleotide
      sequence

<400> SEQUENCE: 11
cccagaagcu gcgaacugu                                                 19

<210> SEQ ID NO 12
<211> LENGTH: 19
<212> TYPE: RNA
<213> ORGANISM: Artificial
<220> FEATURE:
<223> OTHER INFORMATION: Artificially synthesized oligonucleotide
      sequence

<400> SEQUENCE: 12
gucaccgccg ccuaccaca                                                 19

<210> SEQ ID NO 13
<211> LENGTH: 19
<212> TYPE: RNA
<213> ORGANISM: Artificial
<220> FEATURE:
<223> OTHER INFORMATION: Artificially synthesized oligonucleotide
      sequence

<400> SEQUENCE: 13
cgccguacca ggacaccau                                                 19

<210> SEQ ID NO 14
<211> LENGTH: 21
<212> TYPE: RNA
<213> ORGANISM: Artificial
<220> FEATURE:
<223> OTHER INFORMATION: Artificially synthesized oligonucleotide
      sequence

<400> SEQUENCE: 14
aaggcguaua caggaacaau a                                              21
```

METHOD FOR SUPPRESSING RECEPTOR TYROSINE KINASE-MEDIATED PRO-SURVIVAL SIGNALING IN CANCER CELL

CROSS REFERENCE TO RELATED APPLICATIONS

This application is a National Stage of International Application No. PCT/JP2011/080083 filed Dec. 26, 2011, claiming priority based on Japanese Patent Application No. 2010-290373 filed Dec. 27, 2010, the contents of all of which are incorporated herein by reference in their entirety.

TECHNICAL FIELD

The present invention relates to a method for suppressing receptor tyrosine kinase-mediated pro-survival signaling in a cancer cell by targeting ROR1, a screening method for a compound capable of suppressing the signaling, a method for producing a drug for suppressing the signaling, and a drug for suppressing the signaling.

BACKGROUND ART

Lung cancer is a main cause of cancer deaths in economically well-developed countries. Above all, adenocarcinoma is a histological subtype that occurs most frequently.

The present inventors have previously reported that sustained expression of TTF-1, a lineage-specific transcription factor important for lung branching morphogenesis and physiological functions, is closely linked to lung adenocarcinoma (NPL 1). In addition, other three groups have also reached the same conclusion that TTF-1 is a lineage-survival oncogene through, for example, genome-scale searching of focal genome abnormalities in lung adenocarcinoma (NPLs 2 to 4). Since TTF-1 is essential for surfactant-protein production and physiological functions in normal adult lungs, identifying downstream molecules involved in lineage-specific survival signaling by TTF-1 is important for development of novel treatment methods.

As a result of the effort to identify such downstream molecules, the present inventors have succeeded in identifying an ROR1 (receptor tyrosine kinase-like orphan receptor 1) gene as a gene whose expression is induced by TTF-1. Then, the inventors have revealed that it is possible to inhibit the growth of specific cancer cells by suppressing the ROR1 gene expression (PTL 1).

Nevertheless, until now, there have been very little findings about the mechanism of how ROR1 suppresses cancer cell growth.

CITATION LIST

Patent Literature

[PTL 1] International Publication No. WO2010/008069

Non Patent Literatures

[NPL 1] Tanaka, H et al., Cancer Res, 2007, vol. 67, pp. 6007 to 6011
[NPL 2] Kendall, J et al., Proc Natl Acad Sci USA, 2007, vol. 104, pp. 16663 to 16668
[NPL 3] Weir, B A et al., Nature, 2007, vol. 450, pp. 893 to 898
[NPL 4] Kwei, K A et al., Oncogene, 2008, vol. 27, pp. 3635 to 3640

SUMMARY OF INVENTION

Technical Problem

The present invention has been made in view of such a circumstance. The object of the present invention is to further elucidate a mechanism of how ROR1 suppresses the cancer cell growth. Another object of the present invention is to provide a screening method for a compound capable of suppressing the mechanism by targeting ROR1 and to provide a drug comprising as an active ingredient the compound capable of suppressing the mechanism.

Solution to Problem

The present inventors have earnestly studied to achieve the above objects. As a result, the inventors have found that suppression of ROR1 function makes it possible to not only induce pro-apoptotic signaling in a cancer cell, but also suppress pro-survival signaling in a cancer cell, which is transmitted by EGFR through c-Src. It has also been found out that suppressing a function of ROR1 makes it possible to suppress pro-survival signaling in a cancer cell, which is transmitted through a binding between ROR1 and EGFR and a binding between EGFR and ErbB3. Further, the present inventors have found out that suppressing a function of ROR1 also effectively suppresses growth of lung cancer cell lines having acquired resistance to an EGFR tyrosine kinase inhibitor by EGFR mutation or HGF-mediated MET activation.

From these findings, the present inventors have revealed that targeting ROR1 enables not only apoptosis induction in a cancer cell but also a suppression of pro-survival signaling in a cancer cell, which is transmitted by receptor tyrosine kinases such as EGFR and MET, and that ROR1 can be an important target for development of cancer cell-growth inhibitor. These discoveries have led to the completion of the present invention.

Hence, the present invention relates to a method for suppressing receptor tyrosine kinase-mediated pro-survival signaling in a cancer cell by targeting ROR1, a screening method for a compound capable of suppressing the signaling, a method for producing a drug for suppressing the signaling, and a drug for suppressing the signaling. More specifically, the present invention provides the following inventions.

(1) A method for suppressing receptor tyrosine kinase-mediated pro-survival signaling in a cancer cell, the method comprising suppressing a function of ROR1.

(2) The method according to (1), wherein the receptor tyrosine kinase is any one of EGFR and MET.

(3) The method according to (1) and (2), wherein the cancer cell is a cancer cell resistant to any one of an EGFR tyrosine kinase inhibitor and a MET tyrosine kinase inhibitor.

(4) The method according to any one of (1) to (3), wherein the function of ROR1 is suppressed by suppressing a binding between ROR1 and c-Src, suppressing phosphorylation of c-Src due to ROR1, suppressing a binding between ROR1 and EGFR, suppressing a binding between EGFR and ErbB3 due to ROR1, suppressing phosphorylation of ErbB3 due to ROR1, suppressing autophosphorylation of ROR1, or suppressing an expression of an ROR1 gene.

(5) A screening method for a compound capable of suppressing receptor tyrosine kinase-mediated pro-survival signaling in a cancer cell, the method comprising:
   (a) a step of bringing a test compound into contact with a system capable of detecting a function of ROR1; and
   (b) a step of selecting a compound having an activity of suppressing a function of ROR1.
(6) The method according to (5), wherein the receptor tyrosine kinase is any one of EGFR and MET.
(7) The method according to any one of (5) and (6), wherein the cancer cell is a cancer cell resistant to any one of an EGFR tyrosine kinase inhibitor and a MET tyrosine kinase inhibitor.
(8) The method according to any one of (5) to (7), wherein the compound having an activity of suppressing a function of ROR1 is selected based on any of a suppression of a binding between ROR1 and c-Src, a suppression of phosphorylation of c-Src due to ROR1, a suppression of a binding between ROR1 and c-Src, a suppression of phosphorylation of c-Src due to ROR1, a suppression of a binding between ROR1 and EGFR, a suppression of a binding between EGFR and ErbB3 due to ROR1, a suppression of phosphorylation of ErbB3 due to ROR1, a suppression of autophosphorylation of ROR1, and a suppression of an expression of an ROR1 gene.
(9) A method for producing a drug for suppressing receptor tyrosine kinase-mediated pro-survival signaling in a cancer cell, the method comprising a step of mixing the compound selected by the screening method according to any one of (5) to (8) with a pharmaceutically acceptable carrier or medium.
(10) A drug for suppressing receptor tyrosine kinase-mediated pro-survival signaling in a cancer cell, the drug comprising as an active ingredient a compound having an activity of suppressing a function of ROR1.
(11) The drug according to (10), wherein the receptor tyrosine kinase is any one of EGFR and MET.
(12) The drug according to any one of (10) and (11), wherein the cancer cell is a cancer cell resistant to any one of an EGFR tyrosine kinase inhibitor and a MET tyrosine kinase inhibitor.
(13) The drug according to any one of (10) to (12), wherein the compound having an activity of suppressing a function of ROR1 is any of a compound having an activity of suppressing a binding between ROR1 and c-Src, a compound having an activity of suppressing phosphorylation of c-Src due to ROR1, a compound having an activity of suppressing a binding between ROR1 and c-Src, a compound having an activity of suppressing phosphorylation of c-Src due to ROR1, a compound having an activity of suppressing a binding between ROR1 and EGFR, a compound having an activity of suppressing a binding between EGFR and ErbB3 due to ROR1, a compound having an activity of suppressing phosphorylation of ErbB3 due to ROR1, a compound having an activity of suppressing autophosphorylation of ROR1, and a compound having an activity of suppressing an expression of an ROR1 gene.

Advantageous Effects of Invention

The present invention makes it possible to suppress pro-survival signaling in a cancer cell, which is transmitted by a receptor tyrosine kinase, by suppressing a function of ROR1. Suppressing a function of ROR1 suppresses pro-survival signaling in a cancer cell and simultaneously brings about pro-apoptotic signaling through p38 and FOXO1. Accordingly, suppressing a function of ROR1 makes it possible to effectively suppress cancer cell growth. Moreover, suppressing a function of ROR1 also enables a suppression of pro-survival signaling in a cancer cell having acquired resistance to a receptor tyrosine kinase inhibitor such as an EGFR tyrosine kinase inhibitor; hence, targeting ROR1 enables efficient development of therapeutic drugs for refractory cancers. ROR1 demonstrates its function by signal transduction through a binding with a downstream molecule such as c-Src and phosphorylation thereof; accordingly, for example, compounds, which inhibit a binding between ROR1 and c-Src, or inhibit phosphorylation of c-Src due to ROR1, are strong candidates for such therapeutic drugs. Further, ROR1 binds to another receptor tyrosine kinase such as EGFR, and functions in phosphorylation reactions involved in an activated state of these receptor tyrosine kinases and the downstream signal transduction. Thus, compounds capable of inhibiting a binding between ROR1 and another receptor tyrosine kinase such as EGFR, compounds capable of inhibiting a binding between other receptor tyrosine kinases (for example, a binding between EGFR and ErbB3) due to ROR1, compounds capable of inhibiting phosphorylation of other receptor tyrosine kinases such as ErbB3 due to ROR1, or other similar compounds, are also strong candidates for such therapeutic drugs.

DESCRIPTION OF EMBODIMENTS

Figure 1:
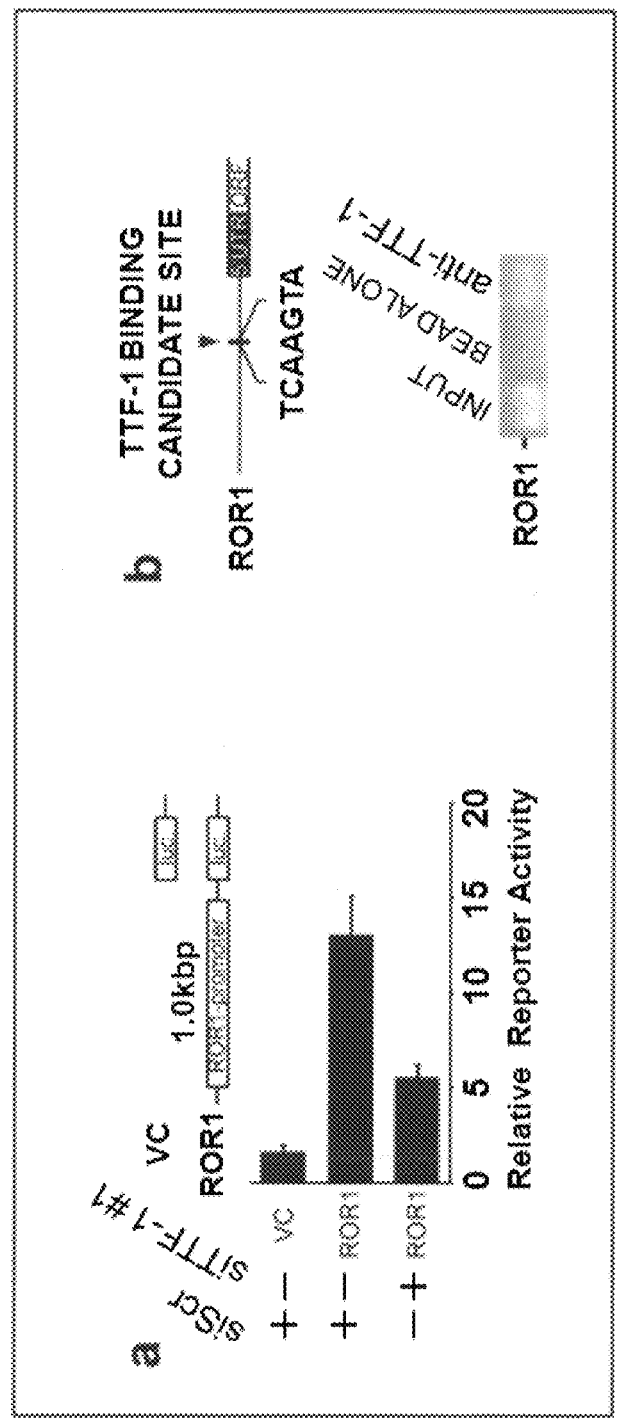
FIG. 1 is a figure to illustrate the result of a luciferase reporter assay and a chromatin immunoprecipitation (ChIP) assay on an ROR1 promoter region. a is a graph for illustrating that a luciferase (Luc.) activity under control of the ROR1 promoter was reduced in accordance with TTF-1 suppression in TTF-1-stably expressing HPL1D cells (stable TTF-1 transfectant of HPL1D) (mean±standard deviation (n=3)). b is a photograph for illustrating an expected site where TTF-1 binds to the ROR1 promoter (TTF-1 binding candidate site) and the ChIP assay showing that TTF-1 had a binding ability to the ROR1 promoter.

The present invention provides a method for suppressing pro-survival signaling in a cancer cell, which is transmitted by a receptor tyrosine kinase, the method characterized by comprising suppressing a function of ROR1.

In the present invention, "receptor tyrosine kinase-mediated pro-survival signaling in a cancer cell" means signaling transmitted in a phosphorylation reaction by receptor tyrosine kinases and a series of downstream molecules as a result of binding of various growth factors (such as EGF, PDGF, FGF, HGF, insulin-like growth factor) to receptors having a tyrosine kinase activity (receptor tyrosine kinases), the signaling inducing an intracellular environment for gene expression, metabolism, and so forth in the cancer cell to be in a circumstance favoring anti-apoptosis and pro-survival. The PI3K/AKT pathway located downstream of the receptor tyrosine kinase is a typical pro-survival signaling pathway, and plays many functions for promoting cancer cell survival. For example, the phosphorylation, due to AKT activated by PI3K, suppressing functions of FOXO family transcription factors and the like, is known to suppress a gene expression involved in apoptosis induction and play an important role in the cell survival.

In the present invention, a "receptor tyrosine kinase" is not particularly limited, as long as the pro-survival signaling is induced through the activation of the receptor tyrosine kinase. Examples thereof include molecules belonging to the EGFR (Epidermal Growth Factor Receptor) family, MET, and the like.

The receptor tyrosine kinase generally undergoes dimerization by a ligand stimulus (binding), which triggers the activation (Yarden, Y et al, Nat Rev Cancer, 2009, vol. 9, pp. 463 to 475). For example, when a ligand EGF binds to EGFR, the conformation of an extracellular domain changes to undergo dimerization with another receptor, and the two receptors phosphorylate each other; hence, a so-called transactivation occurs. The receptor tyrosine kinase having tyrosine phosphorylated in this manner is in an activated state, and intracellular signaling is transmitted to a downstream molecule which plays a role in the signal transduction.

In the present invention, examples of the molecules belonging to the EGFR family include EGFR (ErbB1), Her2 (ErbB2), ErbB3, and ErbB4 (Yarden, Y et al., Nat Rev Cancer, 2009, vol. 9, pp. 463 to 475).

There are multiple ligands for each of the aforementioned molecules other than Her2. Binding of a ligand to an extracellular domain of each receptor induces homodimerization or heterodimerization of the receptor molecules, and cytoplasmic tyrosine kinase domains activated. For example, the expression of EGFR is detected in non-small-cell lung carcinoma at a high frequency, and the gene amplification also takes place in approximately 10% of the cases. Moreover, a point mutation or a deletion mutation of a tyrosine kinase domain specific to lung adenocarcinoma enhances the kinase activity of EGFR, and cancer survival signaling is transmitted through heterodimerization mainly by EGFR and ErbB3. Cancer cells having such a mutation are highly sensitive to EGFR kinase inhibitors (gefitinib, erlotinib, and the like) and anti-EGF receptor antibodies having an antagonistic action (cetuximab). Meanwhile, for example, when EGFR has a double mutation secondarily occurring at T790M, or when the gene of another receptor tyrosine kinase MET is amplified or a ligand HGF thereof is overexpressed, survival signaling is transmitted from MET instead of EGFR and ErbB3 in some cases. This brings about a major clinical problem that the cancer cells acquire resistance to the inhibitors. Overexpression of EGFR due to the gene amplification is observed also in oral cancer, esophageal cancer, brain tumor, and so forth.

Her2 does not have a ligand but is known to have a structure resembling a ligand-binding state stably. Her2 is overexpressed in breast cancer and ovarian cancer at a high frequency often together with the gene amplification, and also serves as a poor prognosis factor. A typical example of a molecularly targeted drug targeting Her2 is Herceptin.

ErbB3 itself has quite a low kinase activity, but has a role of efficiently activating downstream signaling molecules when its tyrosine is phosphorylated upon formation of a heterodimer with EGFR. Particularly, p85, one of PI3K subunits, binds to phosphorylated ErbB3, and survival signaling is transmitted through the PI3K-AKT axis. Expressions of the ErbB3 receptor and the ligand are often increased in breast cancer, ovarian cancer, and lung cancer. The ErbB3 receptor and a ligand are related to the invasion, metastasis, and reduction in the survival rate of individuals. Moreover, ErbB3 is also related to resistance of lung cancer to gefitinib, resistance of colon cancer and head and neck cancers to cetuximab, resistance of breast cancer to trastuzumab, and the like.

The mutation of ErbB4 is observed in lung cancer, stomach cancer, and brain tumor, but the relation to the malignant progression of the disease conditions has not been found unlike the other EGFR family members.

MET is a receptor tyrosine kinase with a ligand hepatocyte growth factor (HGF), and involved in cell survival, growth, migration, morphogenesis, and so on. MET is formed of two subunits α and β from the precursor protein. MET binds to the ligand HGF, and is activated through the dimerization, and thereby signaling involved in the aforementioned biological activities is transmitted. For example, it is believed that a conversion of dependent survival signaling from survival signaling transmitted by the EGFR family (particularly, EGFR and ErbB3) to survival signaling by activated MET through the PI3K-AKT axis leads to resistance acquisition of cancer cells to EGF receptor kinase inhibitors such as gefitinib. The MET activation occurs by MET gene amplification, overexpression of the ligand HGF, and the like. Moreover, the expression of MET is observed in many cancers such as breast cancer and colorectal cancer, and MET is deeply involved in survival, growth, invasion, and metastasis of cancer cells (Trusolino, L et al., Nat Rev Mol Cell Biol, 2010, vol. 11, pp. 834 to 848).

In the present invention, "ROR1" is one of receptor tyrosine kinases. The analysis on the knockout mice has suggested that ROR1 be involved in bone formation, heart development, and the like (Nomi, M et al., Mol Cell Biol, 2001, vol. 21, pp. 8329 to 8335). Moreover, recently, there have been reported that ROR1 is overexpressed in chronic lymphocytic leukemia (Fukuda, T et al., Proc Natl Acad Sci USA, 2008, vol. 105, pp. 3047 to 3052) and overexpressed in cells of particular breast cancers (WO2005/100605). Further, the comprehensive functional screening targeting kinase genes using Hela cells derived from cervical cancer and an RNAi method has suggested that ROR1 be involved in Hela cell survival (MacKeigan, JP et al., Nat Cell Biol, 2005, vol. 7, pp. 591 to 600).

In the present invention, suppressing a function of ROR1 suppresses the pro-survival signaling in a cancer cell, which is transmitted by the receptor tyrosine kinase. Herein, the term "suppress" means not only a complete suppression (i.e., inhibition) but also a partial suppression. Moreover, the phrase "suppressing a function of ROR1" includes both a suppression of an ROR1 activity and a suppression of an expression thereof.

The present invention has found out that ROR1 binds to and phosphorylates c-Src. Further, the present invention has found out that ROR1 binds to EGFR, promotes a binding between EGFR and ErbB3, and promotes phosphorylation of ErbB3. Thus, in the present invention, the "suppression of an ROR1 activity" is preferably (i) a suppression of a binding between ROR1 and a downstream molecule such as c-Src, (ii) a suppression of phosphorylation of a downstream molecule such as c-Src due to ROR1, (iii) a suppression of a binding between ROR1 and a receptor tyrosine kinase such as EGFR, (iv) a suppression of a binding between other receptor tyrosine kinases (for example, a binding between EGFR and ErbB3) due to ROR1, and (v) a suppression of phosphorylation of a receptor tyrosine kinase such as ErbB3 due to ROR1. In addition, since ROR1 is known to autophosphorylate (Forrester, W C et al., Cell Mol Life Sci, 2002, vol. 59, pp. 83 to 96), (vi) a suppression of autophosphorylation of ROR1 is also preferable mode of suppressing a function of ROR1.

In the present invention, examples of the "cancer cell" serving as a target, the pro-survival signaling for which is suppressed by suppressing the ROR1 function, include cells of cancers such as lung cancer, pancreatic cancer, malignant mesothelioma, breast cancer, colorectal cancer, oral cancer, and esophageal cancer, but are not limited thereto. Examples of species from which the cancer cell is derived include human, monkey, mouse, rat, guinea pig, pig, cattle, sheep, goat, and the like, but are not limited thereto. Suppressing a function of ROR1 makes it possible to cause death of a cancer cell resistant to an EGFR tyrosine kinase inhibitor. Accordingly, the present invention is preferably applicable to such refractory cancer treatments. Examples of the EGFR tyrosine kinase inhibitor include gefitinib, erlotinib, EKB-569, lapatinib, canertinib, HKI-272, BIBW2992, PF-00299804, and the like. Furthermore, suppressing a function of ROR1 makes it possible to suppress pro-survival signaling from a MET receptor tyrosine kinase. Accordingly, the present invention is preferably applicable also to treatments of cancers resistant to MET tyrosine kinase inhibitors such as PHA665752, SU11274, and ARQ197.

In order to suppress a function of ROR1 in a cancer cell, a compound capable of suppressing a function of ROR1 can be acted on the cancer cell. In the present invention, examples of the "compound capable of suppressing a function of ROR1" include an anti-ROR1 protein antibody capable of binding to ROR1 and having an activity of suppressing the function, an RNA capable of binding to a transcription product of the ROR1 gene, a peptide having a dominant negative phenotype over an ROR1 protein, a low-molecular-weight compound capable of binding to an ROR1 protein, and the like, which are described later. These compounds are allowed to act on cancer cells through addition to a medium or injection into cultured cells in a case where the cancer cells are cultured, or through administration to a living body by an administration method such as parenteral administration such as intravenous injection or oral administration in a case where the cancer cells are in a living body. It is possible to produce these compounds by methods known to those skilled in the art, and to select one having a desired activity by a screening method of the present invention described below.

The present invention also provides a screening method for a compound capable of suppressing receptor tyrosine kinase-mediated pro-survival signaling in a cancer cell. One embodiment of the screening method of the present invention is a method comprising: a step of bringing a test compound into contact with a system capable of detecting a function of ROR1 (for example, a system capable of detecting a sample containing ROR1 or an expression of an ROR1 gene); and a step of selecting a compound having an activity of suppressing a function of ROR1.

The test compound used in the screening method of the present invention is not particularly limited. Examples thereof include an expression product from a gene library, a synthetic low-molecular-weight compound library, a peptide library, a substance released from a bacterium, a liquid extract and a culture supernatant of cells (microorganisms, plant cells, animal cells), a purified or partially purified polypeptide, an extract derived from a marine organism, plant or animal, soil, and a random phage peptide display library. Further, the examples include an anti-ROR1 protein antibody, a peptide having a dominant negative phenotype over an ROR1 protein, and an RNA capable of binding to a transcription product of the ROR1 gene, which are described later. Moreover, the examples include a compound having a structure capable of binding to the ROR1 protein, which is designed based on the structure of the ROR1 protein.

One embodiment of the screening method of the present invention is a method, wherein the compound having an activity of suppressing a function of ROR1 is selected based on a suppression of a binding between ROR1 and a downstream signaling molecule represented by c-Src. Specifically, this method is a method comprising: a step of bringing ROR1 into contact with a signaling molecule such as c-Src in the presence of the test compound; a step of detecting a binding between ROR1 and them; and a step of selecting a compound having an activity of suppressing the binding.

This method can be carried out in an in vitro binding assay, for example, ELISA (enzyme-linked immunosorbent assay) using a purified ROR1 protein and c-Src purified or in a cell liquid extract, or a GST pull-down assay described in the present Examples. Specifically, His-labeled c-Src and GST-labeled ROR1 conjugated with affinity beads are brought into contact with each other in a buffer to which the test compound has been added; after washing, c-Src binding to ROR1 is detected using an anti-His antibody. If the amount of c-Src detected is smaller than the amount detected in the absence of the test compound, the test compound is evaluated as having an activity of suppressing a binding between ROR1 and c-Src. Besides, methods utilizing, for example, immunoprecipitation, yeast two-hybrid system, FRET (fluorescence resonance energy transfer), or surface plasmon resonance, or other similar methods can be used in the present invention.

ROR1 and c-Src used in this method do not necessarily have to be complete proteins, and may be peptides containing binding sites of the two. For example, an SH3 domain region of c-Src can be used. Examples of species from which ROR1 and c-Src are derived include human, monkey, mouse, rat, guinea pig, pig, cattle, sheep, goat, and the like, but are not limited thereto.

Typical examples of ROR1 used in the present invention include a protein (gene) specified under GenBank ACCESSION No. NP_005003 (NM_005012), when derived from human, and a protein (gene) specified under GenBank ACCESSION No. NP_038873 (NM_013845), when derived from mouse.

Moreover, typical examples of c-Src used in the present invention include a protein (gene) specified under GenBank ACCESSION No. NP_005408 (NM_005417), when derived from human, and a protein (gene) specified under GenBank ACCESSION No. NP_033297 (NM_009271), when derived from mouse.

Another embodiment of the screening method of the present invention is a method, wherein the compound capable of suppressing a function of ROR1 is selected based on phosphorylation of a substrate (for example, c-Src) due to ROR1. Specifically, this method is a method comprising: a step of bringing ROR1 into contact with a substrate in the presence of the test compound; a step of detecting phosphorylation of the substrate due to ROR1; and a step of selecting a compound having an activity of suppressing the phosphorylation.

This method can be carried out in, for example, an in vitro kinase assay using ELISA. As the substrate that phosphorylates due to ROR1, it is possible to use a c-Src protein or a partial peptide thereof, or a protein that may serve as a substrate of the tyrosine kinase or a partial peptide thereof (for example, a gastrin peptide containing a tyrosine residue). In this method, for example, in a plate coated with streptavidin, a purified ROR1 protein, a biotinylated substrate, and a test compound are mixed together and incubated, and then a phosphorylation amount of the substrate is detected using an HRP-labeled anti-phosphorylated tyrosine antibody with a microplate reader. An inhibitory ratio of the ROR1 kinase activity by the test compound can be calculated on the basis of a relative phosphorylation amount detected in the presence and absence of the test compound. If the phosphorylation amount of the substrate detected in the presence of the test compound is smaller than the amount detected in the absence of the test compound, the test compound is evaluated as having an activity of suppressing phosphorylation of a substrate due to ROR1.

Meanwhile, this method can be carried out in, for example, a western blotting analysis using an anti-phosphorylated c-Src antibody as described in the present Examples. In an exemplary method in which the substrate is c-Src, an anti-c-Src antibody is added to a cell lysate of cells expressing endogenous ROR1 and c-Src (for example, NCI-H1975 cells) for immunoprecipitation. The immunoprecipate is incubated in a phosphorylation buffer, and subjected to SDS-PAGE. Then, a western blotting analysis is performed using an anti-phosphorylated c-Src antibody, and the phosphorylation of c-Src is detected. If the phosphorylation amount of c-Src detected is smaller than the amount detected in the absence of the test compound, the test compound is evaluated as having an activity of suppressing phosphorylation of c-Src due to ROR1.

Another embodiment of the screening method of the present invention is a method, wherein the compound capable of suppressing a function of ROR1 is selected based on autophosphorylation of ROR1. Specifically, this method is a method comprising: a step of detecting autophosphorylation by ROR1 in the presence of the test compound; and a step of selecting a compound having an activity of suppressing the phosphorylation. This method can be carried out in, for example, enzyme-linked immunosorbent assay (ELISA), western blotting analysis, In-Cell Western analysis, or the like using an anti-phosphorylated ROR1 antibody. Meanwhile, after immunoprecipitation with an anti-ROR1 antibody, a western blotting analysis may be performed using an anti-phosphorylated tyrosine antibody; alternatively, after immunoprecipitation with an anti-phosphorylated tyrosine antibody, a western blotting analysis may be performed using an anti-ROR1 antibody. If the amount of autophosphorylation of ROR1 detected is smaller than the amount detected in the absence of the test compound, the test compound is evaluated as having an activity of suppressing autophosphorylation of ROR1.

Another embodiment of the screening method of the present invention is a method, wherein the compound having an activity of suppressing a function of ROR1 is selected based on a suppression of a binding between ROR1 and a receptor tyrosine kinase such as EGFR, a suppression of a binding between other receptor tyrosine kinases (for example, a binding between EGFR and ErbB3) due to ROR1, and a suppression of phosphorylation of a receptor tyrosine kinase such as ErbB3 due to ROR1.

Regarding the binding between ROR1 and another receptor tyrosine kinase such as EGFR, it is possible to perform an in vitro binding assay, for example, ELISA (enzyme-linked immunosorbent assay) using a purified ROR1 protein or a partial peptide thereof (for example, a cysteine-rich domain (CRD) of the ROR1 protein) and another receptor tyrosine kinase purified or in a liquid cell extract, a GST pull-down assay, or an immunoprecipitation-western blotting (IP-WB) analysis described in the present Examples. In an exemplary method in which another receptor tyrosine kinase is EGFR, His-labeled EGFR and affinity beads coated with GST-labeled ROR1 are brought into contact with each other in a buffer to which the test compound has been added; after washing, EGFR binding to ROR1 is detected using an anti-His antibody. If the amount of EGFR detected is smaller than the amount detected in the absence of the test compound, the test compound is evaluated as having an activity of suppressing a binding between ROR1 and EGFR. Besides, methods utilizing, for example, immunoprecipitation, yeast two-hybrid system, FRET (fluorescence resonance energy transfer), or surface plasmon resonance, and other similar methods can also be used.

The detection of phosphorylation of another receptor tyrosine kinase due to ROR1 can be carried out by an in vitro kinase assay or a western blotting analysis using an anti-phosphorylated ErbB3 antibody or the like as in the above-described case of detecting phosphorylation of c-Src due to ROR1.

EGFR, ErbB3, and the like used in this method do not necessarily have to be complete proteins. Examples of species from which EGFR, ErbB3, and the like are derived include human, monkey, mouse, rat, guinea pig, pig, cattle, sheep, goat, and the like, but are not limited thereto.

Typical examples of EGFR used in the present invention include a protein (gene) specified under GenBank ACCESSION No. NP_005219 (NM_005228), when derived from human, and a protein (gene) specified under GenBank ACCESSION No. NP_997538 (NM_207655), when derived from mouse.

Moreover, typical examples of ErbB3 used in the present invention include a protein (gene) specified under GenBank ACCESSION No. NP_001973 (NM_001982), when derived from human, and a protein (gene) specified under GenBank ACCESSION No. NP_034283 (NM_010153), when derived from mouse.

Another embodiment of the screening method of the present invention is a method, wherein the compound capable of suppressing a function of ROR1 is selected based on a suppression of an expression of an ROR1 gene. An example of this method is a method comprising: a step of providing a system capable of detecting an expression of an ROR1 gene (for example, a cell or a liquid cell extract having a DNA, in which a reporter gene is operably linked downstream of a promoter region of the ROR1 gene); a step of bringing a test compound into contact with the system to detect an expression of the reporter gene; and a step of selecting a compound capable of suppressing the expression. Herein, the phrase "operably linked" refers to linking of the reporter gene to the promoter region of the ROR1 gene in such a manner that the expression of the reporter gene is induced by binding a transcription factor to the promoter region of the ROR1 gene.

This method can be carried out in, for example, a luciferase reporter assay described in the present Examples. Specifically, a vector containing a luciferase gene linked downstream of the promoter region of ROR1 is introduced into HPL1D cells having a TTF-1 gene introduced and stably expressed, and the test compound is acted on the cells to then measure the luciferase activity. If the luciferase activity detected is lower than the activity detected in the absence of the test compound, the test compound is evaluated as having an activity of suppressing an expression of an ROR1 gene.

As an embodiment utilizing the system capable of detecting an expression of an ROR1 gene other than the method for utilizing the reporter system, a method for directly detecting an expression of an ROR1 gene is also utilizable in the present invention. An example of this method is a method comprising: a step of bringing a test compound into contact with a cell expressing an ROR1 gene; a step of detecting an expression of the ROR1 gene in the cell; and a step of selecting a compound capable of suppressing the expression. In a case where the gene expression is detected at a transcription level, examples of such a method include northern blotting, RT-PCR, dot blot, and the like. In a case where the gene expression is detected at a translation level, examples of the method include ELISA, radioimmunoassay, immunoblotting, immunoprecipitation, and the like. If the expression of the ROR1 gene detected is lower than the expression detected in the absence of the test compound, the test compound is evaluated as having an activity of suppressing an expression of an ROR1 gene.

The compound selected by the above-described screening methods may be mixed with a pharmaceutically acceptable carrier or medium to produce a drug for suppressing receptor tyrosine kinase-mediated pro-survival signaling in a cancer cell. Thus, the present invention provides a method for producing a drug for suppressing receptor tyrosine kinase-mediated pro-survival signaling in a cancer cell, the method comprising a step of mixing the compound selected by the screening method with a pharmaceutically acceptable carrier or medium. Examples of the carrier or medium include a surfactant, an excipient, a colorant, a flavoring, a preservative, a stabilizer, a buffer, a suspension, an isotonic agent, a binder, a disintegrator, a lubricant, a fluidity improver, a taste masking agent, and the like, but are not limited thereto. It is possible to use other commonly-used carriers or media as appropriate. Specific examples thereof include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium chain triglyceride, polyoxyethylene hydrogenated castor Oil 60, white sugar, carboxymethyl cellulose, corn starch, inorganic salts, and the like.

Moreover, the present invention provides a drug for suppressing receptor tyrosine kinase-mediated pro-survival signaling in a cancer cell, the drug comprising as an active ingredient a compound having an activity of suppressing a function of ROR1. Examples of the compound having an activity of suppressing a function of ROR1 include a compound having an activity of suppressing a binding between ROR1 and a downstream signaling molecule represented by c-Src, a compound having an activity of suppressing phosphorylation of a substrate such as c-Src due to ROR1, a compound having an activity of suppressing autophosphorylation of ROR1, a compound having an activity of suppressing a binding between ROR1 and another receptor tyrosine kinase such as EGFR, a compound having an activity of suppressing a binding between other receptor tyrosine kinases (for example, a binding between EGFR and ErbB3) due to ROR1, a compound having an activity of suppressing phosphorylation of another receptor tyrosine kinase such as ErbB3 due to ROR1, and a compound having an activity of suppressing an expression of an ROR1 gene.

Specific examples of the compound having an activity of suppressing a function of ROR1 include an anti-ROR1 protein antibody, an RNA capable of binding to a transcription product of the ROR1 gene, a peptide having a dominant negative phenotype over an ROR1 protein, a low-molecular-weight compound capable of binding to an ROR1 protein, and the like.

The anti-ROR1 protein antibody may be a polyclonal antibody, a monoclonal antibody, or a functional fragment of an antibody. Moreover, the "antibody" includes all classes and subclasses of immunoglobulins. The "functional fragment" of an antibody means apart (partial fragment) of an antibody, which specifically recognizes the ROR1 protein. Specific examples thereof include Fab, Fab', F(ab')2, variable region fragment (Fv), a disulfide bonded Fv, a single chain Fv(scFv), a sc(Fv)2, a diabody, a polyspecific antibody, polymers thereof, and the like.

Moreover, the anti-ROR1 protein antibody includes a chimeric antibody, a humanized antibody, a human antibody, and functional fragments of these antibodies. For administration as a therapeutic drug to human, the antibody of the present invention is desirably a chimeric antibody, a humanized antibody, or a human antibody from the viewpoint of side effect reduction.

In the present invention, a "chimeric antibody" is an antibody obtained by linking a variable region of an antibody of one species to a constant region of an antibody of another species. A chimeric antibody can be obtained as follows, for example. Specifically, a mouse is immunized with an antigen. A portion corresponding to an antibody variable part (variable region) which binds to the antigen is cut out from a gene of a monoclonal antibody of the mouse. The portion is linked to a gene of a constant part (constant region) of an antibody derived from human bone marrow. This is incorporated into an expression vector, which is then introduced into a host for the production of a chimeric antibody (for example, Japanese Unexamined Patent Application Publication No. Hei 8-280387, U.S. Pat. No. 4,816,397, U.S. Pat. No. 4,816,567, U.S. Pat. No. 5,807,715). Moreover, in the present invention, a "humanized antibody" is an antibody obtained by grafting (CDR grafting) a gene sequence of an antigen-binding site (CDR) of a non-human-derived antibody onto a human antibody gene. The preparation methods are known (see, for example, EP239400, EP125023, WO90/07861, WO96/02576). In the present invention, a "human antibody" is an antibody, all regions of which are derived from human. In preparing a human antibody, it is possible to utilize a transgenic animal (for example, a mouse) capable of producing a repertoire of a human antibody by immunization. Preparation methods for a human antibody are known (for example, Nature, 1993, 362, 255-258, Intern. Rev. Immunol, 1995, 13, 65-93, J. Mol. Biol, 1991, 222, 581-597, Nature Genetics, 1997, 15, 146-156, Proc. Natl. Acad. Sci. USA, 2000, 97: 722-727, Japanese Unexamined Patent Application Publication No. Hei 10-146194, Japanese Unexamined Patent Application Publication No. Hei 10-155492, Japanese Patent No. 2938569, Japanese Unexamined Patent Application Publication No. Hei 11-206387, International Application Japanese-Phase Publication No. Hei 8-509612, International Application Japanese-Phase Publication No. Hei 11-505107).

Furthermore, the anti-ROR1 protein antibody includes antibodies whose amino acid sequences are modified without impairing desirable activities. An amino acid sequence mutant can be prepared by introduction of a mutation into a DNA encoding an antibody chain or by peptide synthesis. A site of the antibody where the amino acid sequence is modified may be a constant region of a heavy chain or a light chain of the antibody or a variable region (framework region and CDR) thereof, as long as the resulting antibody has activities equivalent to those before the modification. It is conceivable that modification on an amino acid other than CDR has a relatively small influence on binding affinity for an antigen. As of now, there are known screening methods for antibodies whose binding activity (affinity) for an antigen has been enhanced by modifying an amino acid of CDR (PNAS, 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21: 345-351 (2008)).

The number of amino acids modified is preferably 10 amino acids or less, more preferably 5 amino acids or less, and most preferably 3 amino acids or less (for example, 2 amino acids or less, or 1 amino acid). The amino acid modification is preferably conservative substitution. In the present invention, the "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), sulfur-containing amino acids (cysteine, methionine), amino acids having an amide group (asparagine, glutamine), an amino acid having an imino group (proline), and amino acids having an aromatic group (phenylalanine, tyrosine, tryptophan). The antigen-binding activity can be evaluated, for example, through analysis using a flow cytometer, ELISA, western blotting, immunoprecipitation, or the like.

Furthermore, in the present invention, for the purpose of increasing the stability of the antibody or other purposes, an amino acid subjected to deamidation or an amino acid adjacent to the amino acid subjected to the deamidation may be substituted with a different amino acid to suppress the deamidation. Moreover, the stability of the antibody can also be increased by substituting glutamic acid with a different amino acid. The present invention also provides an antibody thus stabilized.

The modification of the antibody may be a modification on post-translational process of the antibody, for example, the change in the number of sites of glycosylation or in location of the glycosylation. This can improve, for example, the ADCC activity of the antibody. Glycosylation of the antibody is typically N-linked or O-linked glycosylation. The glycosylation of the antibody greatly depends on host cells used for expression of the antibody. The glycosylation pattern can be modified by known methods such as introduction or deletion of a certain enzyme involved in carbohydrate production (Japanese Unexamined Patent Application Publication No. 2008-113663, U.S. Pat. No. 5,047,335, U.S. Pat. No. 5,510,261, U.S. Pat. No. 5,278,299, International Publication No. WO99/54342).

When used in a cancer treatment, the anti-ROR1 protein antibody may be bound to a substance, such as a cytotoxic agent, for the cancer treatment. By using such an antibody, a so-called missile therapy is possible.

Examples of the RNA capable of binding to a transcription product of the ROR1 gene include a complementary dsRNA (double-stranded RNA) to a transcription product of the gene encoding the ROR1 protein or a DNA encoding the dsRNA. In addition, such a dsRNA may have part or all of an RNA substituted with an artificial nucleic acid such as PNA (polyamide nucleic acid, peptide nucleic acid), LNA (registered trademark, locked nucleic acid, Bridged Nucleic Acid), ENA (registered trademark, 2'-O,4'-C-Ethylene-bridged nucleic acids), GNA (Glycerol nucleic acid), or TNA (Threose nucleic acid).

The DNA encoding the dsRNA comprises: an antisense DNA encoding an antisense RNA for any region of the transcription product (mRNA) of the target gene; and a sense DNA encoding a sense RNA for any region of the mRNA. The antisense RNA and the sense RNA can be expressed by the antisense DNA and the sense DNA, respectively. Moreover, the dsRNA can be prepared by these antisense RNA and sense RNA.

As the configuration to incorporate the dsRNA expression system into a vector or the like, the antisense RNA and the sense RNA may be expressed from the same vector, or the antisense RNA and the sense RNA may be expressed from different vectors, respectively. As the configuration in which the antisense RNA and the sense RNA are expressed from the same vector, for example, an antisense RNA expression cassette and a sense RNA expression cassette are constructed, in each of which a promoter capable of expressing a short RNA, such as a pol III system, is linked upstream of the antisense DNA or the sense DNA, and these cassettes are inserted into the vector in the same direction or opposite directions.

Moreover, it is also possible to construct an expression system in which the antisense DNA and the sense DNA are arranged in opposite directions in such a manner as to face each other on the different strands. This construct includes: a single double-stranded DNA (siRNA-encoding DNA) in which an antisense RNA-encoding strand is paired with a sense RNA-encoding strand; and promoters facing each other on both sides of the DNA so that the antisense RNA and the sense RNA can be expressed from the respective strands. In this case, in order to avoid addition of extra sequences downstream of the sense RNA and the antisense RNA, it is preferable to provide a terminator at the 3' end of each of the strands (the antisense RNA-encoding strand, the sense RNA-encoding strand). As the terminator, a sequence of four or more consecutive A (adenine) bases, or the like can be used. In addition, in this palindromic expression system, the type of the two promoters is preferably different.

Meanwhile, as the configuration in which the antisense RNA and the sense RNA are expressed from different vectors, for example, an antisense RNA expression cassette and a sense RNA expression cassette are constructed, in each of which a promoter capable of expressing a short RNA, such as a pol III system, is linked upstream of the antisense DNA or the sense DNA, and these cassettes are incorporated into different vectors. Note that those skilled in the art could prepare the dsRNA by chemically synthesizing the strands.

The dsRNA used in the present invention is preferably a siRNA or a shRNA (short hairpin RNA). A siRNA means a double-stranded RNA made of short strands in such a range that no toxicity is demonstrated within a cell. Meanwhile, a shRNA means a single-stranded RNA in which a sense RNA and an antisense RNA are arranged with a spacer sequence therebetween. Hydrogen bonds are formed between the sense RNA and the antisense RNA in a cell or the like, and the spacer sequence has a hairpin structure. A siRNA can be formed from the shRNA as the hairpin structure is cut out in the cell.

Further, the length of the dsRNA is not particularly limited, as long as the expression of the target gene can be suppressed and no toxicity is demonstrated. The length is for example, 15 to 49 base pairs, preferably 15 to 35 base pairs, and more preferably 21 to 30 base pairs.

The DNAs encoding the dsRNAs do not necessarily have to have completely the same base sequence as that of the target gene, but the homology of the sequence is at least 70% or more, preferably 80% or more, and further preferably 90% or more (for example, 95%, 96%, 97%, 98%, 99% or more). The homology of the sequences can be determined with a BLAST program. The dsRNA is particularly preferably a siRNA described in the present Examples.

In the present invention, examples of another form of the "RNA capable of binding to a transcription product of the ROR1 gene" include a DNA (antisense DNA) encoding an antisense RNA complementary to the transcription product of the ROR1 gene, and a DNA encoding an RNA (ribozyme) having a ribozyme activity of specifically cleaving the transcription product of the ROR1 gene.

Additionally, the peptide having a dominant negative phenotype over an ROR1 protein in the present invention can be prepared as, for example, an ROR1 protein or a partial peptide thereof, which are modified so that the tyrosine kinase activity can be suppressed; an ROR1 protein or a partial peptide thereof, which are modified to block bindings between ROR1 and downstream molecules represented by Src as well as activations of the downstream molecules; an ROR1 protein or a partial peptide thereof (for example, a cysteine-rich domain (CRD) of the ROR1 protein), which are modified to block bindings between ROR1 and receptor tyrosine kinases represented by EGFR as well as activations thereof; or a protein or a peptide, which compete with a binding site on ROR1 for binding a substrate and other receptor tyrosine kinases.

Furthermore, the low-molecular-weight compound capable of binding to an ROR1 protein in the present invention can be identified, for example, from a low-molecular-weight compound library or the like according to the above-described screening of the present invention, and prepared by synthesis methods known to those skilled in the art.

The drug of the present invention may comprise other ingredients in addition to the compound having an activity of suppressing a function of ROR1 as the active ingredient. Examples of the other ingredients include pharmaceutically acceptable carrier and medium described above.

EXAMPLES

Hereinafter, the present invention will be described more specifically based on Examples. However, the present invention is not limited to the following Examples.

<Materials and Methods>

(1) Cell Lines and Reagents

Human lung adenocarcinoma cell lines, NCI-H1975, NCI-H820, PC-9, NCI-H358, NCI-H441, and NCI-H23 were purchased from American Type Culture Collection. SK-LC-5 and SK-LU-1 cell lines were provided from Lloyd J. Old (Memorial Sloan-Kettering Cancer Center). Then, these cell lines were maintained with 10% fetal bovine serum (FBS)-supplemented RPMI 1640 (manufactured by Invitrogen Corporation). Moreover, an immortalized lung epithelial cell line HPL1D was maintained according to the method described in "Masuda, A. et al., Cancer Res, 1997, vol. 57, pp. 4898 to 4904."

Gefitinib was purchased from Biaffin GmbH & CoKG. recombinant EGF and recombinant HGF were obtained from Sigma-Aldrich Co. and PeroTech Inc., respectively.

The following antibodies were purchased from the following companies, respectively.

Anti-ROR1 (#4102), anti-c-Src (36D10, #2109), anti-phospho-c-Src (Y416, #2101), anti-PTEN (138G6, #9559), anti-phospho-PTEN (5380/T382/T383, #9554), anti-phospho-AKT (T308, C31E5E, #2965), anti-phospho-AKT (S473, #9271), anti-FOXO1 (C29H4, #2880), anti-phospho-FOXO1 (S256, #9461), anti-phospho-p38 (T180/Y182, #9211), anti-caspase-3 (#9662), and anti-phospho-ErbB3 (Y1289, #4791) were purchased from Cell Signaling Technology, Inc.

Anti-TTF-1 (8G7G3/1, M3575) was purchased from DAKO. Anti-α-tubulin (T5192) was purchased from Sigma-Aldrich Co.

Anti-c-myc (9E10, sc-40), anti-Tyr (PY20, sc-508), and anti-ErbB3 (c-17, sc-285) were purchased from Santa Cruz Biotechnology, Inc.

Anti-GST (3B2, M071-3) was purchased from MBL CO., LTD.

Anti-ROR1 (TA302193) was purchased from Origene Technologies, Inc.

Anti-PI3K (p85) (06-497) was purchased from MILLIPORE CORPORATION.

Anti-mouse IgG and anti-rabbit IgG were purchased from Cell Signaling Technology, Inc.

(2) Constructs

A construct for expressing a full-length human TTF-1 cDNA in pCMV-puro, and a construct for expressing a double-stranded short hairpin RNA (shRNA) against TTF-1 expression in pH1RNAneo were constructed according to the description of "Tanaka, H et al., Cancer Res, 2007, vol. 67, pp. 6007 to 6011."

Moreover, a full-length human ROR1 cDNA (manufactured by OriGene Technologies, Inc.) was inserted into a pCMVpuro vector. Then, the sequence of an open reading frame (ORF) of the construct (pCMVpuro-ROR1) thus obtained was accurately checked. Further, a myc-labeled ROR1 expression vector (pIRES2puro-ROR1-myc) was prepared.

In addition, a full-length human EGFR cDNA (RIKEN) was inserted into the pCMVpuro vector. Then, the sequence of an open reading frame (ORF) of the construct (pCMVpuro-EGFR) thus obtained was accurately checked. pNeoMSV-c-Src wild-type (WT), constitutive active (CA), and kinase dead (KD) were provided from Dr. Tony Hunter (the Salk Institute). These inserts were introduced into a pCMVpuro vector.

Moreover, pRC-CMV-c-Src wild type (WT), Δ15-84 (Δ15), Δ90-144 (Δ90), and Δ150-246 (Δ150) were provided from Dr. Sanford Shattil (the University of California, San Diego).

Further, pIRES2puro-ROR1-ΔN-myc and pIRES2puro-ROR1-ΔC-myc were prepared by a molecular biological method using restriction enzymes.

Furthermore, pIRES2puro-ROR1-ΔIg-myc, pIRES2puro-ROR1-ΔCRD-myc, pIRES2puro-ROR1-ΔKringle-myc, pIRES2puro-ROR1-ΔIg+CRD-myc, pIRES2puro-ROR1-ΔCRD+Kringle-myc, and pIRES2puro-ROR1-ΔIg+CRD+Kringle-myc were prepared by in vitro mutagenesis using a KOD-plus-DNA polymerase (TOYOBO CO., LTD.). Primers used in each preparation are shown below:

```
ΔIg forward primer:
                                    (SEQ ID NO: 1)
5'-GTGGTTTCTTCCACTGGAGTCTTGT-3', ΔIg reverse primer:
                                    (SEQ ID NO: 2)
5'-CGTGGTGATGTTATTCATTGGTTCA-3', ΔCRD forward primer:
                                    (SEQ ID NO: 3)
5'-ATCCGGATTGGAATTCCCATGGCAG-3', ΔCRD reverse primer:
                                    (SEQ ID NO: 4)
5'-GAATCCATCTTCTTCATACTCATCT-3', ΔKringle forward primer:
                                    (SEQ ID NO: 5)
5'-GATTCAAAGGATTCCAAGGAGAAGA-3',
and ΔKringlereverse primer:
                                    (SEQ ID NO: 6)
5'-CTTGTGATTTTTATTTATAGGATCT-3'.
```

(3) Microarray Analysis

A gene was introduced into the HPL1D cell line using FuGENE6 (Invitrogen Corporation). After puromycin treatment to establish stable expression cells of each of HPL1D-TTF-1-stably expressing cells (stable clone) and HPL1D-VC stable clone.

RNAs were extracted from the HPL1D-TTF-1-stably expressing cells and HPL1D-VC stable clone, and cRNAs were prepared using a low RNA fluorescent linear amplification kit (manufactured by Agilent Technologies, Inc.) according to the manufacture's instruction, and labeled with Cy3 or Cy5 (manufactured by GE Healthcare).

The labeled cRNAs were hybridized to Agilent 44K Human whole genome microarray, and then placed in a DNA microarray scanner (manufactured by Agilent Technologies, Inc.). Incidentally, the expression profiling analysis was performed twice.

(4) Western Blotting Analysis and Immunoprecipitation-Western Blotting Analysis

A western blotting analysis and an immunoprecipitation-western blotting analysis were performed according to standard methods using Immobilon-P filters (manufactured by Millipore Corporation) and an enhanced chemiluminescence system (manufactured by GE Healthcare). In order to check a physiological binding between ROR1 and c-Src, pIRES2puro-ROR1 was expressed alone or co-expressed with various c-Src-expressing constructs such as wild type (WT), Δ15-84 (Δ15), Δ90-144 (Δ90), and Δ150-246 (Δ150). From these, the cells were collected 24 hours after the transfection, and the immunoprecipitation-western blotting analysis was performed. Moreover, the pCMV-puro-TTF-1 was transiently transfected into HPL1D cells, and induction of ROR1 expression was checked by the western blotting analysis.

In order to check a physiological binding between ROR1 and EGFR, pCMVpuro-EGFR was co-expressed with various ROR1-deletion mutant expression constructs such as pIRES2puro-VC, pIRES2puro-ROR1-WT, ΔN, ΔC, ΔIg, ΔCRD, ΔKringle, ΔIg+CRD, ΔCRD+Kringle, or ΔIg+CRD+Kringle. From these, culture solutions were removed 24 hours after the transfection. After washing with PBS, a culture solution not containing serum (FBS: fetal bovine serum) was substituted, and the resultant was further cultured for 24 hours. Then, after treated with 20 ng/ml of EGF, the cells were collected, and the immunoprecipitation-western blotting analysis was performed.

(5) Immunofluorescence Staining

The cells were subjected to a standard immunofluorescence staining method, and observed using an LSM5 Pascal confocal laser scanning microscope (manufactured by Carl Zeiss AG).

(6) Luciferase Reporter Assay

An ROR1 luciferase reporter construct was prepared using a pGL4 pasic reporter vector (manufactured by Promega KK) and a PCR product obtained by amplifying a 1.0-kb genome fragment of a promoter region of ROR1. Note that the luciferase reporter activity was detected according to the description of "Osada, H et al., Cancer Res, 2001, vol. 61, pp. 8331 to 8339." Moreover, the luciferase reporter activity was measured using Dual-reporter assay system (manufactured by Promega KK). Further, the firefly luciferase activity was normalized based on the *Renilla* luciferase activity.

(7) Chromatin Immunoprecipitation (ChIP) Assay

After SK-LC-5 cells were cross-linked using 1% formamide and collected, the chromatins were sheared by ultrasonication into 500 to 600 bp on average. Then, immunoprecipitation was performed using a TTF-1 specific antibody. After reverse cross-linking, the chromatins obtained by the immunoprecipitation were subjected to PCR using primers for amplifying the ROR1 promoter region. Note that these primers were as follow.

```
                                    (SEQ ID NO: 7)
Forward primer: 5'-TCTCTCTGAGCCTCGGTTTC-3'

(SEQ ID NO: 8)
Reverse primer: 5'-CCCCCACACTCCTCAAACT-3'.
```

(8) RNA Interference (RNAi) on Human ROR1, TTF-1, and PTEN

In order to perform RNAi, the following RNA oligomers were obtained from QIAGEN and Sigma-Aldrich Co.

```
                                    (SEQ ID NO: 9)
5'-CAGCAAUGGAUGGAAUUUCAA-3': siROR1#1

(SEQ ID NO: 10)
5'-CCCAGUGAGUAAUCUCAGU-3': siROR1#2

(SEQ ID NO: 11)
5'-CCCAGAAGCUGCGAACUGU-3': siROR1#3

(SEQ ID NO: 12)
5'-GUCACCGCCGCCUACCACA-3': siTTF-1#1

(SEQ ID NO: 13)
5'-CGCCGUACCAGGACACCAU-3': siTTF-1#2

(SEQ ID NO: 14)
5'-AAGGCGUAUACAGGAACAAUA-3': siPTEN
```

In addition, AllStars Negative Control siRNA (siScr) was obtained from QIAGEN.

The siRNAs (each 20 nM) were transfected using Lipofectamine RNAiMAX (manufactured by Invitrogen Corporation) according to the instruction of the maker. Then, 72 hours after the transfection, the cells were collected for a western blotting analysis.

Moreover, 5 days after the transfection, the cell growth and apoptosis induction were measured using TetraColor One colorimetoric assay kit (manufactured by Seikagaku Corporation) and in situ cell death detection kit (manufactured by Roche Diagnostics K. K.).

(9) Analysis on Functional Interaction of ROR1 with TTF-1 and c-Src

In order to analyze the effect of endogenous ROR1 expression in lung adenocarcinoma cells in which TTF-1 expression was suppressed, pH1RNAneo-shTTF-1 and pCMVpuro-ROR1 were transfected at a ratio of 1:4 into NCI-H358, followed by neomycin treatment for 2 weeks. Then, the number of colonies was counted. Next, in order to examine a functional interrelation between ROR1 and c-Src, a pCMVpuro vector expressing wild type c-Src (WT) or a pCMVpuro vector expressing constitutively active c-Src (CA) was introduced into NCI-H1975 cells, followed by puromycin treatment for 3 days. Then, a siRNA against ROR1 was introduced. 72 hours after the siRNA introduction, the cells were collected for a western blotting analysis. In addition, 5 days after the siRNA introduction, a MTT assay was conducted.

(10) In Vivo Tumorigenicity Assay

NCI-H1975 cells at $1.0 \times 10^7$ were subcutaneously inoculated into lower flanks of 8-week-old athymic nude mice (manufactured by Japan SLC, Inc.). One week after the inoculation, 1 nmol of the siRNAs (siROR1#1, #2, and #3) and 200 μl of atelocollagen (manufactured by KOKEN CO., LTD.) were mixed together, and injected into tumors having an average volume of 50 $mm^3$. The tumor weights were measured 2 weeks after the siRNA injection to obtain the mean of the data±standard error (SE) (n=7).

In an in vivo tumorigenicity assay using an ROR1-stably expressing line (stable ROR1 transfectant), MSTO-211H cells stably expressed ROR1 or MSTO-211H cells having an empty vector introduced were subcutaneously inoculated at $1.0 \times 10^7$ into lower flanks of 8-week-old athymic nude mice (manufactured by Japan SLC, Inc.) as described above. In this case, 3 weeks after the inoculation, the tumor weights were measured to obtain the mean of the data±standard error (SE) (n=5). Further, expressions of various proteins in the tumors were analyzed by western blotting. Note that all the animal experiments were conducted in compliance with the regulations for animal experiments of Nagoya University.

(11) Combined Effects of ROR1 Suppression with EGF, HGF, and Gefitinib

NCI-H1975 cells and SK-LC-5 cells were treated with 20 nM siROR1 or siScr for 2 days, and serum-starved for 24 hours. After that, these cells in this state were treated with 20 ng/ml of EGF, and analyzed by western blotting and immunofluorescence staining.

NCI-H1975 cells and NCI-H820 cells were treated with 20 nM siROR1 or siScr for 3 days, and treated with 1 μM gefitinib for 6 hours. Then, the cells were collected and subjected to a western blotting analysis. Moreover, as for a MTT assay on these cells, the cells were subjected to siRNA transfection and then treated with 1 μM gefitinib for 4 days, and the measurement was performed.

Similarly, PC9 cells having the siRNA introduced and cultured for 3 days were treated with 1 μM gefitinib and/or 50 ng/ml of HGF for 6 hours. The cells were collected for a western blotting analysis. Moreover, as for a MTT assay on these cells, the cells were subjected to siRNA transfection and then treated with 1 μM gefitinib and/or 50 ng/ml of HGF for 4 days, and the measurement was performed.

(12) Preparation of Recombinant Proteins

GST-labeled ROR1 (intracellular domain) was expressed in Sf9 insect cells (manufactured by Invitrogen Corporation) using Gateway system according to the instruction of the marker. Then, the recombinant GST-labeled ROR1 protein was purified by glutathione-affinity chromatography. A His-labeled c-Src protein and a GST protein were purchased from Invitrogen Corporation and Abnova Corporation, respectively. Recombinant proteins of GST-labeled SH2 region and GST-labeled SH3 region of c-Src were obtained from Marligen Biosciences, Inc. and Jena Bioscience GmbH, respectively.

(13) GST Pull-Down Assay

In a buffer consisting of 20 mM MOPS [pH 7.2], 1 mM dithiothreitol, 5 mM EGTA, 25 mM β-glycerophosphate, 1 mM $Na_3VO_4$, and 75 mM $MgCl_2$, purified His-labeled c-Src was mixed with affinity beads to which recombinant GST- or recombinant GST-labeled ROR1 had been bound. Then, the beads were washed, and the resultant was dissolved in an SDS sample buffer. The eluate was subjected to SDS-PAGE, and then subjected to a western blotting analysis using an anti-GST or anti-His antibody.

A liquid cell extract of NCI-H1975 cells was mixed with affinity beads to which recombinant c-Src proteins of a recombinant GST-labeled SH2 region and a GST-labeled SH3 region had been bound. After washing several times, the resultant was dissolved in an SDS sample buffer. The eluate was subjected to SDS-PAGE, and then subjected to a western blotting analysis using an anti-GST or anti-ROR1 antibody.

(14) In Vitro Kinase Assay

Using liquid extracts of NCI-H23 cells and 293T cells, c-Src was immunoprecipitated. The immunoprecipitate was incubated together with GST or GST-ROR1 in a phosphorylation buffer (25 mM Tris-HCl [pH 7.5], 5 mM $MgCl_2$, 0.5 mM ATP) at 30° C. for 1 hour. Then, a western blotting analysis was performed using an anti-phospho-c-Src antibody.

Moreover, NIH3T3 cells were transfected with pCMVpuro-KD-c-Src, and treated with puromycin for 5 days. The cells were used to immunoprecipitate kinase-dead c-Src for use as a substrate for an ROR1 kinase assay.

Example 1

Identification of ROR1 Involved in Lineage-Specific Survival Signaling by TTF-1

The luciferase reporter assay utilizing a region near 1.0-kb of the human ROR1 gene promoter showed the activation was dependent on TTF-1 (a in FIG. 1). The chromatin immunoprecipitation assay revealed that TTF-1 directly bound to the ROR1 gene promoter (b in FIG. 1). These results indicated that ROR1 was a transcription target of TTF-1.

Example 2

Figure 2:
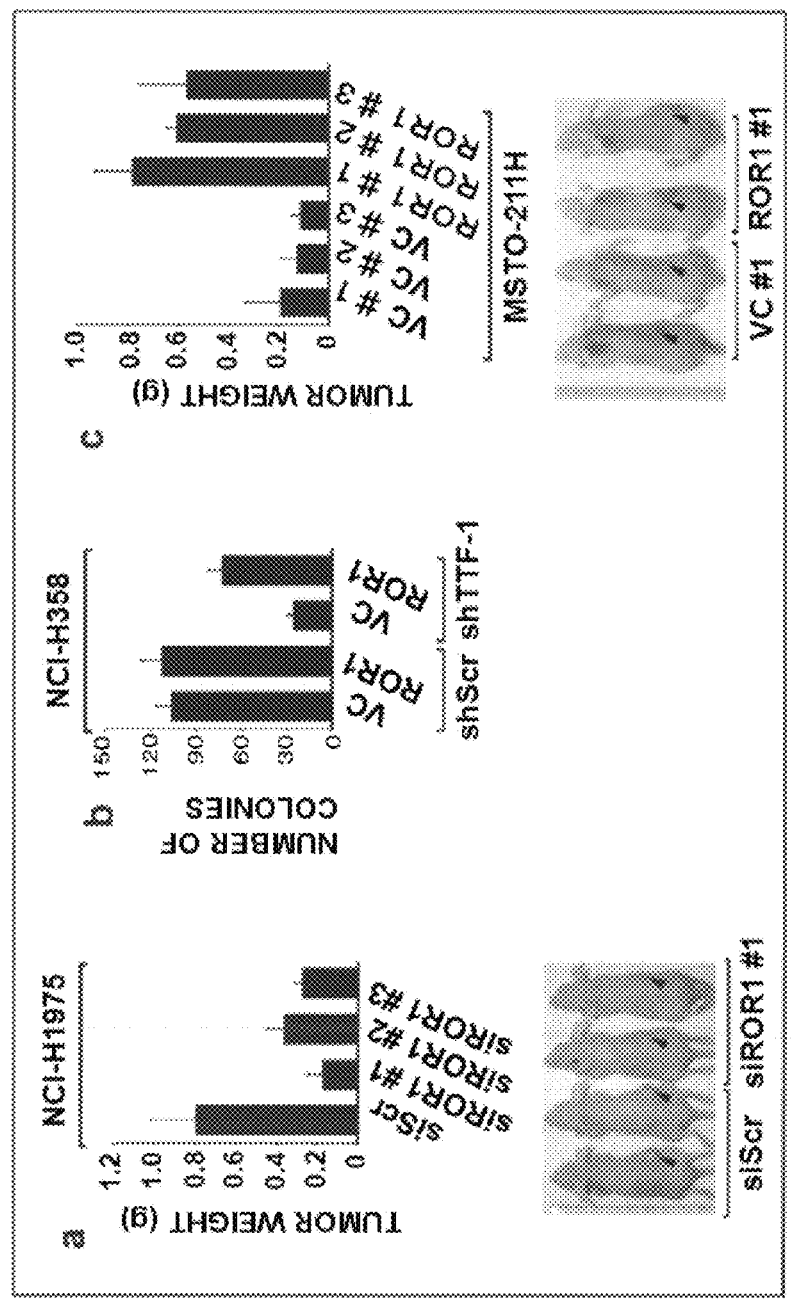
FIG. 2 shows graphs for illustrating that ROR1 was present in signaling downstream by TTF-1 lineage-survival oncogene involved in survival of lung adenocarcinoma. a shows a graph and a photograph for illustrating in vivo. the result of mixing siRNA with atelocollagen, taking photographs 2 weeks after the injection into tumors, and measuring the tumor weights, that is, illustrating the in vivo anti-tumor effect of ROR1 siRNA (mean±standard deviation (n=7)). b is a graph for illustrating the result of counting the number of colonies after 2 weeks after simultaneous introduction of an ROR1 expression vector and a short hairpin RNA expression vector against TTF-1 into TTF-1+/ROR1+NCI-H358 cells. The ROR1 introduction alleviated the growth suppression elicited by TTF-1 shRNA (mean±standard deviation (n=3)). In other words, it was demonstrated that ROR1 played a role in survival signaling transmitted by TTF-1. c shows a graph and a photograph for illustrating that in vivo tumor growth of an ROR1-stably expressing cell line (stable ROR1 transfectant) was enhanced. Note that the top panel shows an average tumor weight 3 weeks after the subcutaneous injection (mean±standard deviation (n=5)), and the bottom panel shows photographs of representative mice 3 weeks after the injection.

Verification of Influence on Lung Adenocarcinoma Cell Growth by ROR1 Expression Suppression or Expression Enhancement The in vivo treatment by administering ROR1 siRNA with atelocollagen into the tumors significantly reduced the growth of the xenograft tumor from NCI-H1975 (a in FIG. 2).

Meanwhile, the growth of the TTF-1$^+$/ROR1$^+$NCI-H358 cells having been suppressed to a substantial degree by the short hairpin TTF-1 (shTTF-1) expression was significantly restored by co-expressing ROR1 (b in FIG. 2). This suggests that ROR1 induced by TTF-1 be a quite important mediator located downstream of survival signaling by TTF-1.

Further, the in vivo growth of the xenograft tumor from the ROR1-negative MSTO-211H cells was enhanced by exogenously expressing ROR1 at a level equivalent to that of the NCI-H358 cells (c in FIG. 2).

Example 3

Identification of Downstream Molecules in ROR1-Mediated Signal Transduction Next, in order to elucidate the ROR1-mediated signal transduction, potential downstream molecules were analyzed by the western blotting analysis.

Figure 3:
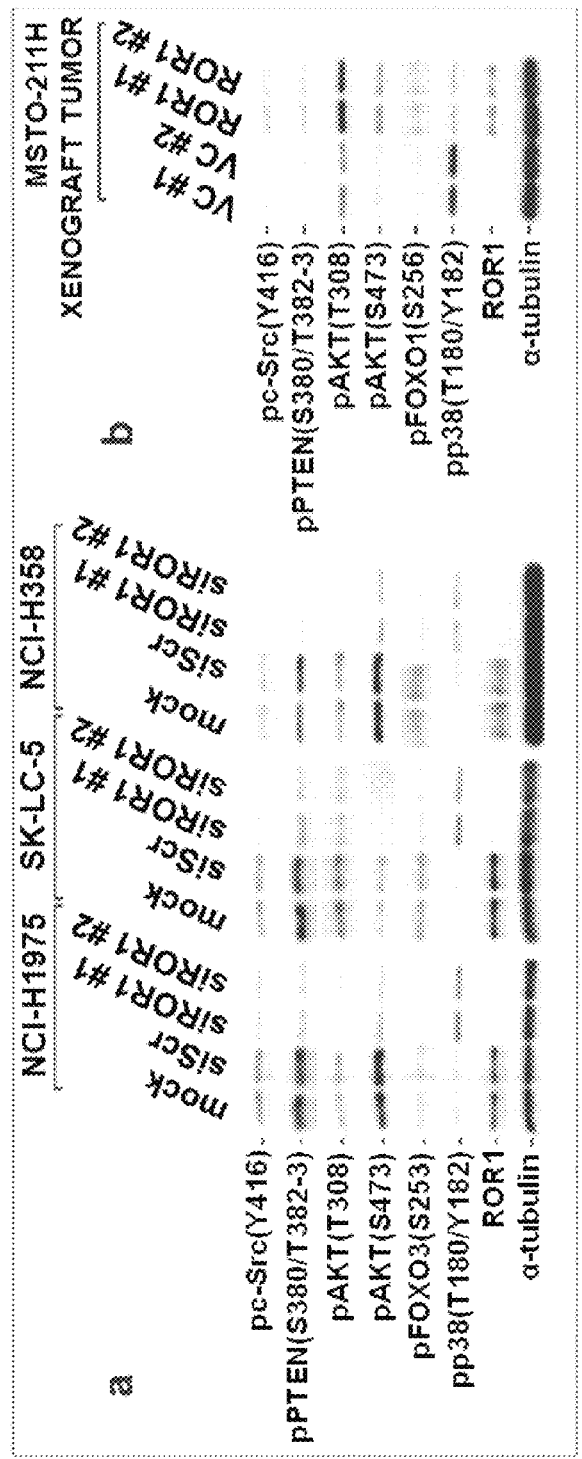
FIG. 3 shows graphs for illustrating that ROR1 contributed to pro-survival signaling maintenance by signal transduction through the c-Src-PTEN axis and had a function of suppressing p38 activation that promotes apoptosis. a is a photograph for illustrating the result of analyzing changes in phosphorylation states of c-Src, PTEN, AKT, FOXO1, and p38 in siROR1-treated cells by western blotting. b is a photograph for illustrating the result of analyzing opposite effects on the phosphorylation states in ROR1-stably expressing cells by western blotting.

Suppressing ROR1 reduced phosphorylation of c-Src, PTEN, AKT, and FOXO1, but enhanced phosphorylation of p38 (a in FIG. 3). Meanwhile, the xenograft tumor derived from ROR1-introduced MSTO-211H cells demonstrated opposite effects (b in FIG. 3).

These findings match an "oncogenic shock" model, in which rapid inhibition of oncogenic signal transduction unbalances pro-survival signaling and pro-apoptotic signaling, consequently leading to cell death.

ROR1-positive lung adenocarcinoma cell lines are dependent on ROR1-mediated survival signaling in this manner. If the signaling is inhibited, apoptotic reactions would be sequentially induced.

Example 4

Verification of Survival Signaling Due to ROR1 Through c-Src

Figure 4:
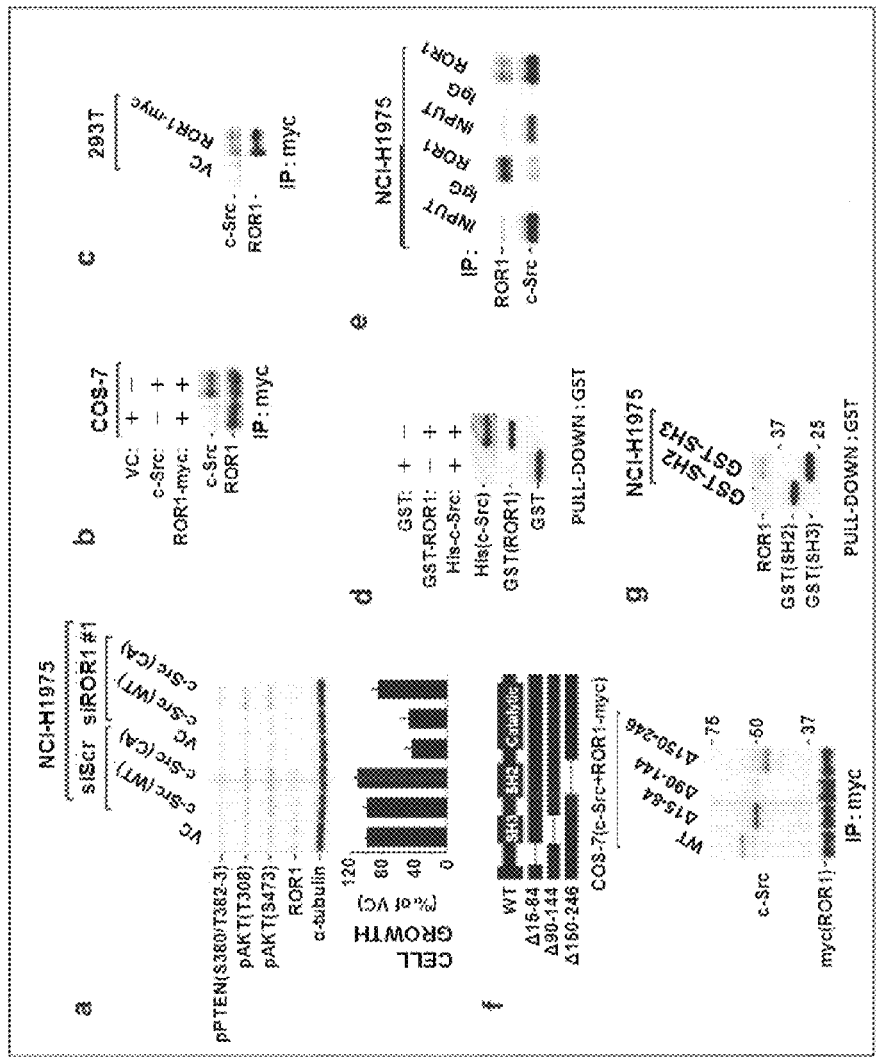
FIG. 4a shows the results of performing a western blotting analysis 72 hours after introduction of siROR1 following previous introduction of c-Src (top panel), and measuring the cell growth by a colorimetric analysis performed 5 days after the siROR1 introduction (bottom panel). Specifically, a shows a photograph and a graph for illustrating that constitutively active c-Src significantly antagonized ROR1 suppression (mean±standard deviation (n=3)), and that c-Src was located downstream. Note that "VC" indicates an empty vector as a control, "WT" indicates wild type c-Src, and "CA" indicates constitutively active c-Src. b is a photograph for illustrating an immunoprecipitation-western blotting (IP-WB) analysis, in which exogenous ROR1 and c-Src were co-immunoprecipitated in COS-7 cells. c is a photograph for illustrating an IP-WB analysis, in which ROR1 and c-Src were co-immunoprecipitated in ROR1-introduced 293T cells. d is a photograph for illustrating an in vitro pull-down assay showing an interaction between a purified ROR1 protein and a c-Src protein. e is a photograph for illustrating an IP-WB analysis using a lysate of NCI-H1975 cells, in which endogenous ROR1 and c-Src were co-immunoprecipitated. Note that "IgG" indicates a negative control. f is a photograph for illustrating the result of analyzing an interaction between ROR1 and the SH3 domain of c-Src by IP-WB, in which myc-labeled ROR1 and various c-Src-deletion mutants were introduced into COS-7 cells. Note that the top panel shows a schematic diagram of the c-Src-deletion mutants. g is a photograph for illustrating an in vitro pull-down assay using a purified GST-labeled c-Src domain, in which endogenous ROR1 bound to the SH3 domain of c-Src, but endogenous ROR1 did not bind to the SH2 domain of c-Src.

Furthermore, focusing on the fact that phosphorylation of the 416th tyrosine of c-Src is increased in ROR1-knockdown cells or ROR1-overexpressing cells, examined was how phosphorylation induced by ROR1 suppression and the cell growth suppression were changed by introducing constitutively active c-Src into NCI-H1975 cells. As a result, it was demonstrated that the introduction of constitutively active c-Src changed the phosphorylation states of PTEN and AKT induced by ROR1 suppression, and remarkably reduced the growth suppression of the NCI-H1975 cells (a in FIG. 4). This suggests that c-Src be involved in at least part of ROR1-mediated survival signal transduction in lung adenocarcinoma.

Next, in order to elucidate a mechanism of how ROR1 controls c-Src, whether or not ROR1 bound to c-Src was examined. As a result, an interaction between ROR1 and c-Src exogenously introduced into COST cells (b in FIG. 4) and an interaction between endogenous c-Src and ROR1 transfected in 293T cells were clearly proved (c in FIG. 4). In addition, the in vitro pull-down assay using a purified ROR1 protein and a c-Src protein demonstrated a direct interaction therebetween (d in FIG. 4). Further, the immunoprecipitation-western blotting (IP-WB) analysis confirmed that endogenous ROR1 and c-Src interacted with each other in NCI-H1975 cells (e in FIG. 4). Moreover, the IP-WB analysis using various c-Src deletion mutants revealed that ROR1 bound to the SH3 domain of c-Src (f in FIG. 4). Furthermore, the GST pull-down assay using a lysate of NCI-H1975 cells also revealed that endogenous ROR1 interacted with the SH3 domain of c-Src (g in FIG. 4).

Example 5

Verification of c-Src Phosphorylation Due to ROR1

Figure 5:
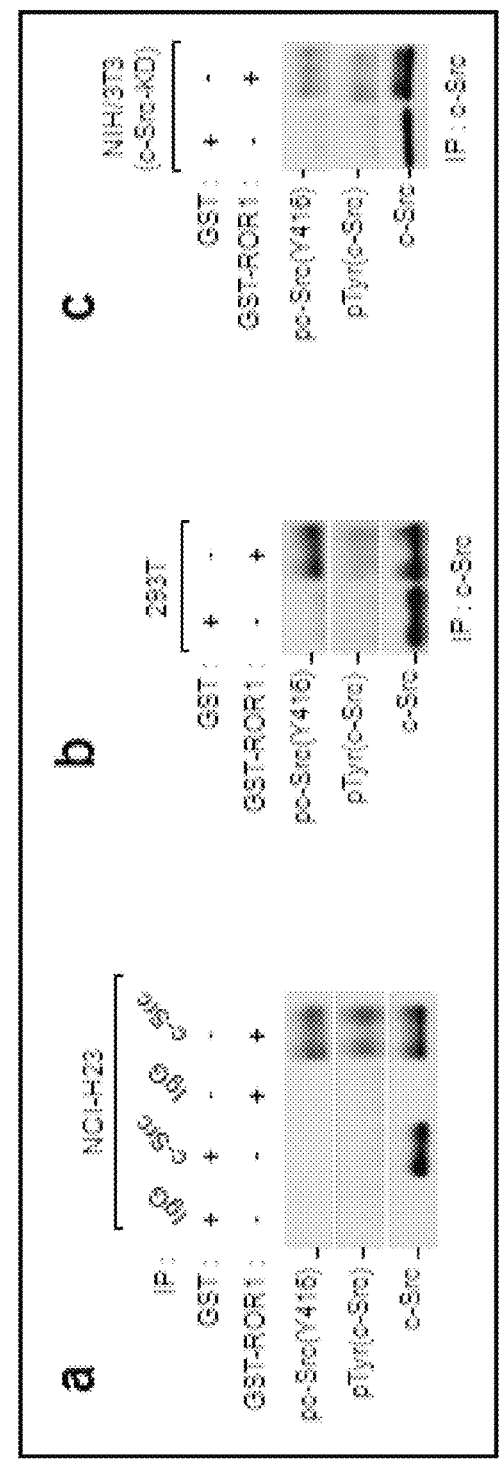
FIG. 5a is a photograph for illustrating the result of an in vitro ROR1 kinase assay, in which c-Src obtained by immunoprecipitation in an ROR1-deficient NCI-H23 lung adenocarcinoma cell line was used as a substrate, that is, illustrating that c-Src was clearly phosphorylated by incubation together with GST-ROR1 in the presence of ATP. b is a photograph for illustrating that c-Src was phosphorylated by an in vitro ROR1 kinase assay, in which c-Src obtained by immunoprecipitation from a lysate of 293T cells was used as a substrate. c is a photograph for illustrating the result of an in vitro ROR1 kinase assay using an immunoprecipitate of kinase-inactive c-Src in NIH3T3 cells, the c-Src having been introduced as a substrate into the cells.

Next, whether or not c-Src was phosphorylated by ROR1 was examined. Specifically, the in vitro ROR1 kinase assay was performed using c-Src as a substrate, in which c-Src was immunoprecipitated from cell lysates of NCI-H23 and 293T cells. The examination result revealed that c-Src was phosphorylated by ROR1 (a in FIG. 5 (NCI-H23 cells) and b in FIG. 5 (293T cells)).

Further, it was confirmed using NIH3T3 cells expressing kinase dead c-Src (c-Src-KD) that the phosphorylation of c-Src was not due to an autophosphorylation reaction of c-Src. Note that c-Src-KD was a substrate having no autophosphorylation ability (c in FIG. 5).

Example 6

Figure 6:
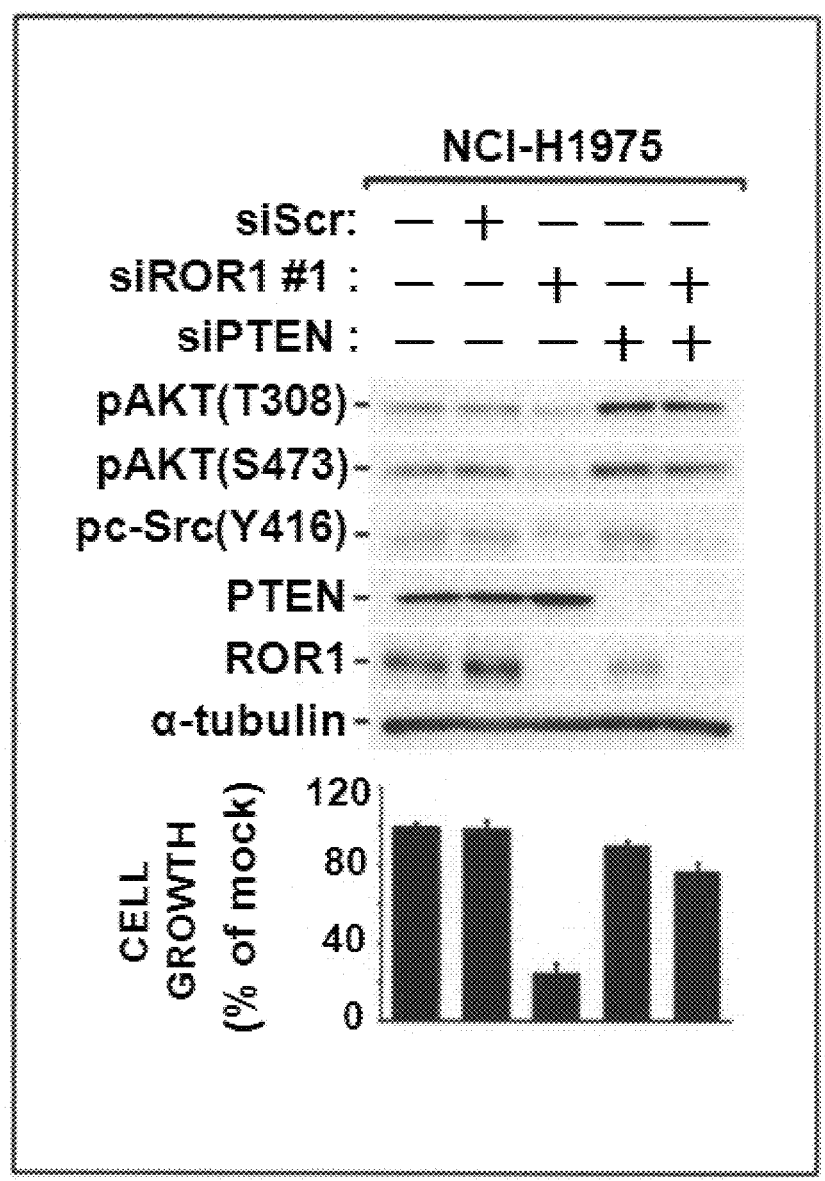
FIG. 6 shows a diagram for illustrating that PTEN was located downstream of ROR1. The top is a photograph for illustrating that ROR1 had an activity of maintaining pro-survival signaling by suppressively controlling PTEN known to be inactivated by c-Src, thereby promoting AKT activation. To put it differently, the photograph illustrates that a combination of siRNA against ROR1 and siRNA against PTEN to suppress expressions of the two restored the AKT phosphorylation. The bottom panel is a graph for illustrating that the resulting effect of suppressing cell growth induced by suppressing ROR1 is alleviated if PTEN is also suppressed (mean±standard deviation (n=3)).

Verification of PTEN Control Due to ROR1 Through c-Src Serving as Survival Signaling c-Src is known to induce an inactivation of PTEN by phosphorylating PTEN. It was revealed that if PTEN was simultaneously suppressed in NCI-H1975 cells, the influence on AKT phosphorylation induced by ROR1 suppression and the consequent growth suppression were almost eliminated (FIG. 6).

Thus, it was revealed that ROR1 bound to c-Src and phosphorylated c-Src, and that c-Src played a very important role of regulating pro-survival signaling through the ROR1-c-Src-PTEN-PI3K-AKT axis in lung adenocarcinoma.

Example 7

Verification of Crosstalk Between ROR1 and ErbB Family

Figure 7:
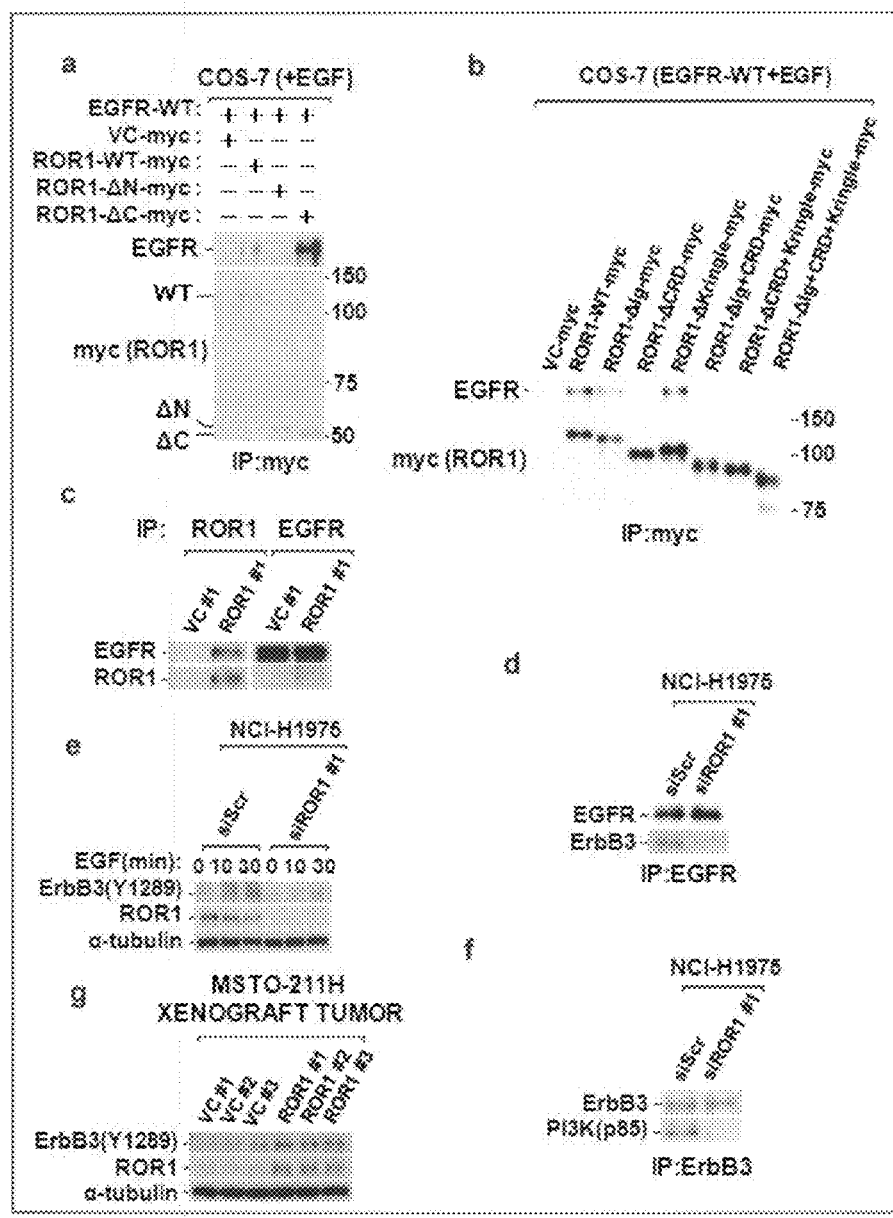
FIG. 7 is a figure to illustrate that an interaction between ROR1 and EGFR is necessary for a phosphorylation reaction of ErbB3. a is a photograph for illustrating that ROR1 and EGFR bound to each other, and that EGFR interacted with an extracellular region of ROR1 under EGF stimulus by an IP-WB analysis using ROR1-deletion mutants. Note that "ROR1-ΔN" indicates a mutant lacking an extracellular region of ROR1, and "ROR1-ΔC" indicates a mutant lacking an intracellular region of ROR1. b is a photograph for illustrating the result of a further detailed analysis on a binding region in the extracellular region of ROR1 binding to EGFR. Specifically, the photograph illustrates that EGFR bound at a cysteine-rich domain (CRD) in the extracellular region of ROR1. Note that, "ROR1-ΔIg" indicates a mutant lacking an Ig domain of ROR1, "ROR1-ΔCRD" indicates a mutant lacking a CRD domain of ROR1, and "ROR1-ΔKringle" indicates a mutant lacking a Kringle domain of ROR1. Moreover, "ROR1-ΔIg+CRD" indicates a mutant lacking the Ig domain and the CRD domain of ROR1, "ROR1-ΔCRD+Kringle" indicates a mutant lacking the CRD domain and the Kringle domain of ROR1, and "ROR1-ΔIg+CRD+Kringle" indicates a mutant lacking the Ig domain, the CRD domain, and the Kringle domain of ROR1. c is a photograph for illustrating an IP-WB analysis using a lysate of ROR1-stably expressing cells, in which endogenous ROR1 and EGFR were co-immunoprecipitated, and the two bound to each other. Note that "VC" is a control cell lysate not having an ROR1 gene introduced. d is a photograph for illustrating the result of an IP-WB analysis using a lysate of NCI-H1975 cells having ROR1 expression suppressed, that is, illustrating that suppressing ROR1 inhibited a binding between endogenous EGFR and ErbB3, which is an important partner molecule of EGFR for heterodimer formation to transmit pro-survival signaling. e is a photograph for illustrating the result of a western blotting analysis on a phosphorylation reaction reflecting an activated state of ErbB3 in ROR1-suppressed NCI-H1975 cells. Specifically, the photograph illustrates that the ErbB3 phosphorylation induced by an EGF treatment was remarkably reduced by suppressing ROR1. f is a photograph for illustrating an IP-WB analysis using the lysate of the NCI-H1975 cells having ROR1 expression suppressed, in which suppressing ROR1 inhibited a binding between endogenous ErbB3 and the p85, subunit of PI3K. The p85 subunit recognized and bound to a phosphorylation site of ErbB3 to transmit pro-survival signaling. g is a photograph for illustrating the result of a western blotting analysis on an increase in the phosphorylation state of ErbB3 in the ROR1-stably expressing cells.

It is well understood that the ErbB family, particularly EGFR and ErbB3, play important roles in survival and growth of lung cancer. Moreover, recently, more importance has been placed on crosstalks among receptor tyrosine kinases. It is believed that receptors are present very close to each other on the cell membrane, and play a role of pro-survival signaling by communicating with each other. Hence, an analysis was performed by the immunoprecipitation-western blotting (IP-WB) method. As a result, it was revealed that ROR1 bound to EGFR under EGF stimulus. Moreover, it was found out that the interaction of the two was such that the binding was achieved at an extracellular region of ROR1 (a in FIG. 7). Further, detailed studies on the binding region of ROR1 revealed that ROR1 and EGFR interacted with each other at a cysteine-rich domain located in the extracellular region of ROR1 (b in FIG. 7). Additionally, the binding between endogenous ROR1 and EGFR was detected by the immunoprecipitation-western blotting (IP-WB) analysis using ROR1-introduced MSTO-211H cells (c in FIG. 7). Furthermore, the study by the IP-WB analysis using lung adenocarcinoma cells NCI-H1975 having ROR1 expression suppressed revealed that suppressing ROR1 inhibited the binding between endogenous EGFR and ErbB3, which was an important partner molecule of EGFR for heterodimer formation to transmit pro-survival signaling (d in FIG. 7). In addition, it was observed that phosphorylation reflecting an activated state of ErbB3 for transmitting pro-survival signaling caused by EGF stimulus was significantly reduced by suppressing an expression of ROR1 in lung adenocarcinoma cells NCI-H1975 (e in FIG. 7). Furthermore, a binding between ErbB3 and the subunit p85 of PI3K, which recognized and bound to a phosphorylation site of ErbB3 to transmit pro-survival signaling, was examined in the lung adenocarcinoma cells NCI-H1975 having ROR1 expression suppressed. As a result, a reduction in the binding between ErbB3 and p85 was revealed (f in FIG. 7). Furthermore, in the xenograft tumor derived from the ROR1-introduced MSTO-211H cells, an increase in the phosphorylation reaction of ErbB3 was observed (g in FIG. 7).

Thus, the followings were revealed. Specifically, ROR1 plays important roles in: the binding and phosphorylation of receptor tyrosine kinases important for pro-survival signal transduction by binding to a receptor tyrosine kinase such as EGFR; the binding between downstream signal transduction factors; and the like. ROR1 is necessary to transmit receptor tyrosine kinase-mediated pro-survival signaling.

Example 8

Verification of Association Between ROR1 and EGFR-Mediated Signal Transduction

It is well understood that EGFR-mediated signal transduction plays an important role in lung cancer growth. Hence, next, an association between EGFR-mediated signal transduction and ROR1 was examined. As a result, it was revealed that suppressing ROR1 remarkably inhibited phosphorylation of c-Src, AKT, and FOXO1 induced by EGF (a in FIG. 8).

Figure 8:
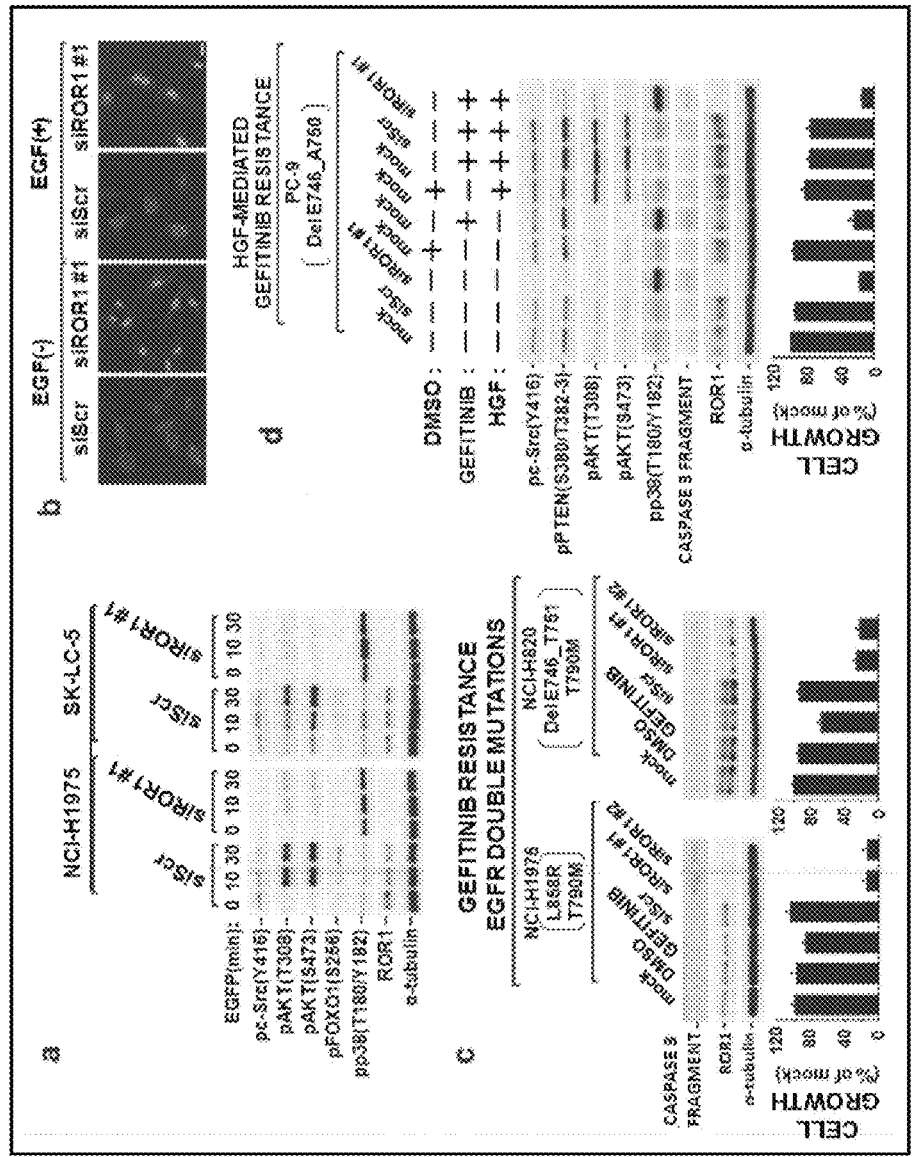
FIG. 8 is a figure to illustrate that ROR1 is necessary to maintain EGFR and MET signal transductions in lung adenocarcinoma. a illustrates the result of a western blotting analysis on potential downstream molecules in SK-LC-5 cells and NCI-H1975 cells having ROR1 suppressed. Specifically, the photograph illustrates that phosphorylation of c-Src, AKT, and FOXO1 induced by an EGF treatment was remarkably reduced by suppressing ROR1. b is a photograph of the result of an immunofluorescence analysis showing that FOXO1, having a cell-death inducing ability and whose function was suppressively regulated by pro-survival signaling transmitted by a receptor tyrosine kinase such as EGFR through AKT, was translocated into the nucleus and in an activated state therein even under EGF treatment in ROR1-suppressed NCI-H1975 cells. Note that the scale bar represents 30 μm. c shows a photograph and a graph for illustrating that suppressing ROR1 induced cell death and inhibited the growth in NCI-H1975 cells and NCI-H820 cells having a T790M EGFR mutation known to confer resistance to gefitinib. Note that, the top panel illustrates the result of a western blotting analysis on an expression of a caspase 3 fragmentation, which reflects induction of cell death. The bottom panel illustrates the result of a colorimetric assay (mean±standard deviation (n=3)). d illustrates the result of analyses by a colorimetric assay and western blotting on ROR1 downstream in ROR1-suppressed PC9 cells treated with gefitinib and/or HGF. Specifically, the photograph and the graph illustrate that, in the PC-9 cells harboring EGFR mutation (E746_A750), AKT phosphorylation for gefitinib resistance induced by HGF-mediated MET activation was significantly reduced by suppressing ROR1, remarkably inhibiting the growth (mean±standard deviation (n=3)).

Further, it was revealed that the nuclear retention of FOXO1, a downstream molecule inactivated by AKT and an apoptosis promoting factor, was induced regardless of the presence or absence of EGF in ROR1-suppressed NCI-H1975 cells; hence, an activation of apoptosis was induced (b in FIG. 8).

Thus, phosphorylation of p38 induced by suppressing ROR1 is not influenced by EGF treatment. This suggests that sustained ROR1 expression be essential for EGFR-mediated pro-survival signal transduction in lung adenocarcinoma and suppression of pro-apoptotic signal transduction.

Example 9

Verification of Effectiveness of ROR1 Suppression in Lung Cancer Cells Resistant to EGFR Tyrosine Kinase Inhibitors NCI-H1975 cells and NCI-H820 cells are cell lines having double mutations of the EGFR gene including a T790M mutation conferring resistance to EGFR tyrosine kinase inhibitors. In any of the cell lines, EGF addition strongly brought about pro-survival signaling; meanwhile, suppressing ROR1 remarkably reduced it and brought about pro-apoptotic signaling, remarkably suppressing the cell growth (c in FIG. 8).

In addition, another mechanism has been recently reported as follows. Overexpression of the ligand HGF of the MET receptor tyrosine kinase and MET gene amplification induce MET activation. This switches dependency target involved in survival from EGFR to MET, thereby conferring resistance to EGFR tyrosine kinase inhibitors (Yano, S et al., Cancer Res, 2008, vol. 68, pp. 9479 to 9487; Turke, A B et al., Cancer Cell, 2010, vol. 17, pp. 77 to 88). Hence, an association between HGF/MET and ROR1 was examined.

As a result, it was revealed that, by HGF treatment, PC9 lung adenocarcinoma cells having EGFR mutation acquired resistance to EGFR tyrosine kinase inhibitors; meanwhile, suppressing ROR1 suppressed pro-survival signaling transmitted by MET (d in FIG. 8).

Thus, it was revealed that ROR1, a downstream molecule of lineage-specific survival oncogene TTF-1, was necessary to maintain pro-survival signaling from other receptor tyrosine kinases such as EGFR and MET, and to suppress pro-apoptotic signaling. Further, this indicates that ROR1 suppression is quite useful as a treatment target for cancer cells having resistance to receptor tyrosine kinase inhibitors such as EGFR and MET.

INDUSTRIAL APPLICABILITY

As has been described above, the present invention makes it possible to not only enhance pro-apoptotic signaling, but also suppress receptor tyrosine kinase-mediated pro-survival signaling in a cancer cell by suppressing a function of ROR1. According to the present invention, suppressing a function of ROR1 also enables a suppression of growth of cancer cells having acquired resistance to inhibitors of receptor tyrosine kinases such as EGFR and MET. Accordingly, the present invention can contribute greatly to development of therapeutic drugs for cancers including refractory cancers.

[Sequence Listing Free Text]
SEQ ID NOs: 1 to 8
<223> Artificially synthesized primer sequence
SEQ ID NOs: 9 to 14
<223> Artificially synthesized oligonucleotide sequence

The invention claimed is:

1. A screening method for a compound capable of suppressing receptor tyrosine kinase-mediated pro-survival signaling in a cancer cell, the method comprising:
   (a) a step of bringing a test compound into contact with a system capable of detecting a function of receptor tyrosine kinase-like orphan receptor 1 (ROR1); and
   (b) a step of selecting a compound having an activity of suppressing a function of ROR1, wherein the compound having an activity of suppressing a function of ROR1 is selected based on any of a suppression of a binding between ROR1 and c-Src, a suppression of phosphorylation of c-Src due to ROR1, a suppression of a binding between ROR1 and EGFR, a suppression of a binding between EGFR and ErbB3 due to ROR1, a suppression of phosphorylation of ErbB3 due to ROR1, and a suppression of autophosphorylation of ROR1.

2. The method according to claim 1, wherein the receptor tyrosine kinase is any one of EGFR and MET.

3. The method according to claim 1, wherein the cancer cell is a cancer cell resistant to any one of an EGFR tyrosine kinase inhibitor and a MET tyrosine kinase inhibitor.

* * * * *